(12) United States Patent
Chang

(10) Patent No.: US 11,915,797 B2
(45) Date of Patent: Feb. 27, 2024

(54) METHODS FOR MANAGING SEQUENCING PILEUPS

(71) Applicant: GRAIL, LLC, Menlo Park, CA (US)

(72) Inventor: Christopher Chang, Palo Alto, CA (US)

(73) Assignee: Grail, LLC, Menlo Park, CA (US)

( * ) Notice: Subject to any disclaimer, the term of this patent is extended or adjusted under 35 U.S.C. 154(b) by 1225 days.

(21) Appl. No.: 16/438,259

(22) Filed: Jun. 11, 2019

(65) Prior Publication Data

US 2020/0013483 A1 Jan. 9, 2020

Related U.S. Application Data

(60) Provisional application No. 62/719,483, filed on Aug. 17, 2018, provisional application No. 62/685,823, filed on Jun. 15, 2018.

(51) Int. Cl.
G16B 50/50 (2019.01)
G16B 30/10 (2019.01)

(52) U.S. Cl.
CPC ............. *G16B 50/50* (2019.02); *G16B 30/10* (2019.02)

(58) Field of Classification Search
None
See application file for complete search history.

(56) References Cited

U.S. PATENT DOCUMENTS

2017/0199764 A1* 7/2017 Tijanic et al. ........ G06F 9/4881

OTHER PUBLICATIONS

Zhang, Overview of Sequence Data Formats, in Statistical Genomics: Methods and Protocols, Mar. 2016, Springer Science+Business Media (Year: 2016).*
Dónaill, On the application of integer arithmetic in nucleotide sequence analysis, Oct. 1995, Computer Applications in the Biosciences 11(5): 567-569 (Year: 1995).*
Li et al., The Sequence Alignment/Map format and SAMtools, Jun. 2009, Bioinformatics 25(16): 2078-2079 (Year: 2009).*
Niemanmaa, Analysing sequencing data in Hadoop: The road to interactivity via SQL [Master's Thesis], Nov. 2013, Aalto University (Year: 2013).*
Creutzberg et al., Algorithms and Data Structures—Part 5: String Matching, May 2015, self-published (accessed via ResearchGate) (Year: 2015).*
Paterson et al., Final Text of DIS 8859-1, 8-bit single-byte coded graphic character sets —Part 1: Latin alphabet No. 1, Nov. 1997, ISO/IEC 8859-1 (Year: 1997).*
Kusswurm et al, Modern X86 Assembly Language Programming, 2014, Apress / Springer Science + Business Media Finance Inc., New York NY. Excerpt of Chapter 5, pp. 133-145 (Year: 2014).*
Hasan et al., Chapter 9: An Overview of Hardware-Based Acceleration of Biological Sequence Alignment, in Computational Biology and Applied Bioinformatics, 2011, Intech (Year: 2011).*
Wilhalm et al., SIMD-Scan: Ultra Fast in-Memory Table Scan using On-Chip Vector Processing Units, Aug. 2009, Proceedings of the VLDB Endowment 2(1): 385-394 (Year: 2009).*
Pedersen, et al., "Mosdepth: quick coverage calculation for genomes and exomes," Bioinformatics, vol. 34, Issue 5, 867-868 (2018).
Quinlan, "BEDTools: a flexible suite of utilities for comparing genomic features," Bioinformatics, vol. 26, Issue 6, 841-842 (2010).

* cited by examiner

*Primary Examiner* — Soren Harward
*Assistant Examiner* — Theodore Charles Striegel
(74) *Attorney, Agent, or Firm* — Sheppard Mullin Richter & Hampton LLP

(57) ABSTRACT

In comparison to conventional sequencing pileup algorithms, the process described herein generates sequencing pileups that contains additional information not typically reported by conventional algorithms while also consuming fewer computational resources (e.g., time, processing power, and memory). First, each of a FASTA reference genome and BAM sequence read files are converted to an internal representation. This enables the rapid iteration across nucleotide bases of the sequence reads to determine support characteristics that summarize information of nucleic acid molecules corresponding to positions across the reference genome. Next, the support characteristics of positions across the reference genome are stored through a memory allocation process that utilizes a first and a second temporary storage. This enables the convenient freeing of one temporary storage while the other temporary storage is being used.

14 Claims, 18 Drawing Sheets
Specification includes a Sequence Listing.

230

Nucleotide bases of converted sequence read file: G A T G C T C G A A G C T N C A Nucleotide bases of converted reference genome file: G A T G C T C G A A G C T G C A

Nucleotide bases
of converted
sequence read file

G A T G C T C G A A G C T N C A

G A T G C T C G A A G C T G C A

Nucleotide
bases of
converted
reference
genome file

Nucleotide bases of converted sequence read file: G A T G C T C G A A G C T N C A ...

Nucleotide bases of converted reference genome file: G A T G C T C G A A G C T G C A ...

FIG. 3E

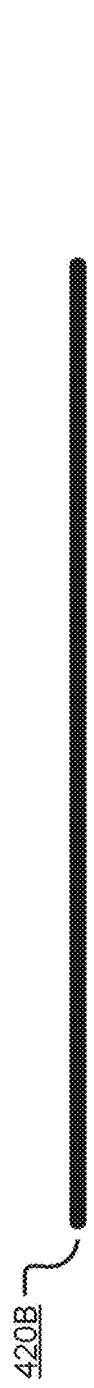
FIG. 4A
FIG. 4B
FIG. 4C

METHODS FOR MANAGING SEQUENCING PILEUPS

CROSS-REFERENCE TO RELATED APPLICATIONS

This application claims the benefit of priority to U.S. Provisional Patent Application No. 62/685,823, filed on Jun. 15, 2018, and entitled "METHODS FOR GENERATION SEQUENCING PILEUPS AND MEMORY MANAGEMENT," and to U.S. Provisional Patent Application No. 62/719,483, filed on Aug. 17, 2018, and entitled "METHODS FOR MANAGING SEQUENCING PILEUPS," the contents of which are herein incorporated by reference in their entirety.

REFERENCE TO SEQUENCE LISTING SUBMITTED VIA EFS-WEB

This application includes an electronically submitted sequence listing in .txt format. The .txt file contains a sequence listing entitled "P0126-US_ST25.txt" created on Sep. 3, 2019 and is 799 bytes in size. The sequence listing contained in this .txt file is part of the specification and is hereby incorporated by reference herein in its entirety.

BACKGROUND

High-throughput DNA sequencers usually produce millions of sequence reads derived from an individual's genome, each sequence read denoting nucleotide bases of a DNA strand of the individual. Sophisticated algorithms are typically used to align these sequence reads to a reference genome to generate a position-based sequencing pileup. Such a sequencing pileup generated for an individual's genome can be used for various purposes, an example of which includes the use of sequencing pileups to determine a likelihood of a presence of cancer in the individual. However, given the large number of aligned reads as well as the number of nucleotide bases in the human genome that are to be analyzed, the implementation of conventional pileup algorithms results in a computationally costly endeavor to generate the sequencing pileup. Pileup algorithms can be improved to reduce the computational costs that are needed to process and analyze aligned reads while simultaneously increasing the amount of information stored in sequencing pileups.

SUMMARY

Disclosed herein are methods for generating and storing sequencing pileups that consume fewer computational resources (e.g., time, processing power, memory, etc.) in comparison to conventional pileup algorithms. Generally, aligned sequence reads derived from a sample obtained from an individual are compared to corresponding reference genome positions to determine support characteristics. Here, support characteristics summarize information of nucleic acid molecules that correspond to a particular position of the reference genome. For example, support characteristics of a position can describe nucleotide bases of DNA molecules that match a nucleotide base at the position of the reference genome as well as nucleotide bases of possibly cancer-related DNA molecules that differ from the nucleotide base at the position of the reference genome. Such support characteristics are stored and included in a sequencing pileup.

A reference genome file, which is commonly expressed in a FASTA format, includes nucleotide bases of a reference genome. The reference genome of the reference genome file is converted from the FASTA format to an internal representation. Additionally, a sequence read file, which is commonly expressed in a binary alignment map (BAM) format, includes nucleotide bases of sequence reads. The sequence read file is converted from the BAM format to the same internal representation, thereby enabling rapid comparison between groups of sequence-read and reference-genome nucleobases. By comparing the two files that are each represented in the internal representation, support characteristics for each genomic position are determined. Here, the position-by-position comparison is performed more rapidly (frequently by more than a factor of 10) than existing methods.

The support characteristics of positions across the reference genome are stored using a memory allocation process that consumes fewer computational resources dedicated to memory allocation operations than conventional algorithms. The memory allocation process employs a ring buffer, a first temporary storage, and a second temporary storage. Here, the implementation of the temporary storages enables the management of support characteristics that are unbounded (e.g., insertions and/or deletions that can each differ in the number of nucleotide bases). The sizes of the ring buffer, first temporary storage, and second temporary storage can be kept smaller than that of the input dataset, thereby minimizing the amount of memory that is needed at any given time. The memory allocation process ensures that the temporary storages are opportunistically freed to effectively manage support characteristics from differing positions.

Generally, the memory allocation process involves partitioning positions across the reference genome into multiple partitions. The memory allocation process is a looping process, where at each loop, the process stores, into persistent storage, support characteristics of genomic positions within two adjacent partitions. At a subsequent loop, the process stores, into persistent storage, supporting characteristics of genomic positions of the next two adjacent partitions. Therefore, over many process loops, the supporting characteristics of genomic positions across the reference genome are stored into persistent storage.

Within each process loop, a fixed-length sliding window is applied along the reference genome within one or both of the two adjacent partitions to define an active interval. Therefore, sequence reads that align with the reference genome within the active interval are analyzed at any given time to determine support characteristics of those genomic positions within the active interval. By defining a size of the active interval, the memory allocation process need only continuously keep track of support characteristics of positions within the active interval, while dynamically allocating support characteristics of prior positions no longer within the active interval to one of the temporary storages.

Specifically, as an active interval is located fully within a first partition, the support characteristics of positions within the active interval are determined, stored in the ring buffer and a first temporary storage. As the active interval is shifted along the reference genome, positions within the first partition are no longer within the active interval. Support characteristics of these positions no longer within the active interval are written from the first temporary storage to persistent storage. This process is iterated until the support characteristics of all positions in the first partition are written to persistent storage.

In the meantime, as the active interval shifts along the reference genome, the active interval enters into a second partition and therefore, support characteristics of positions in the second partition are determined, stored in the ring buffer and a second temporary storage. Thus, as the first temporary storage is occupied with support characteristics of positions in the first partition, the second temporary storage is utilized for storing support characteristics of positions in the second partition. Altogether, support characteristics of positions from differing partitions can be maintained in parallel in different temporary storages.

Upon writing the support characteristics of all positions in the first partition from the first temporary storage to persistent storage, the data in the first temporary storage is stale and no longer needed. Therefore, the first temporary storage is freed and made available for storing additional information, such as, for example, support characteristics of a third partition. Therefore, as the active interval shifts into the third partition, support characteristics of positions within the third partition are stored into the ring buffer and the now-freed first temporary storage. Therefore, as the second temporary storage holds support characteristics of positions in the second partition, the first temporary storage is utilized to manage support characteristics of positions in the third partition. Subsequently, as the active interval exits the second partition, support characteristics of all positions in the second partition have been transferred to persistent storage. Therefore, the information in the second temporary storage is stale and the second temporary storage can be made available for storing additional information, such as support characteristics of a fourth partition. This alternating implementation of the first temporary storage and second temporary storage continues to repeat until support characteristics of positions across all partitions of the reference genome are stored into the persistent storage.

In some embodiments described herein, a method for determining support characteristics of positions across a reference genome comprises accessing a reference genome file comprising the reference genome expressed in a first format, accessing a sequence read file comprising the sequence read expressed in a second format different from the first format, converting the first format of the reference genome in the reference genome file into an internal representation, converting the second format of the sequence read in the sequence read file into the internal representation, and identifying one or more mismatched nucleotide bases by comparing the sequence read expressed in the internal representation to the reference genome expressed in the internal representation.

In some examples, the internal representation represents each nucleotide base using a full byte. In some examples, the first format is a FASTA format. Further, in some examples, converting the first format of the reference genome in the reference genome file into the internal representation comprises accessing a lookup table to lookup M nucleotide bases of the reference genome of the reference genome file in a single clock cycle. In some examples, M=16, 32, or 64 nucleotide bases.

In some examples, the second format is a binary alignment/map (BAM) format. In some examples, converting the second format of the sequence read in the sequence read file into the internal representation comprises extracting a low-order 4-bit value of a byte representing a second nucleotide base and a high-order 4-bit value of the byte representing a first nucleotide base and reordering the low-order 4-bit value and high-order 4-bit value. Further, in some examples, converting the second format of the sequence read in the sequence read file into the internal representation further comprises expanding each of the first 4-bit value and the second 4-bit value into a full byte. In some examples, the extracting, reordering, and the expanding of the first 4-bit value and the second 4-bit value of the byte are altogether performed in parallel in less than a clock cycle per input byte.

In some examples, comparing the sequence read expressed in the internal representation to the reference genome expressed in the internal representation comprises performing one of a bitwise exclusive-or (XOR) or AND-NOT operation to compare N contiguous nucleotide bases. In some examples, performing the bitwise XOR operation comprises accessing a concise idiosyncratic gapped alignment report (CIGAR) string of the sequence read file, wherein the bitwise XOR operation is performed on a segment of nucleotide bases represented by an alignment matching region indicated by the CIGAR string. Further, in some examples, the method includes, responsive to the XOR operation returning a value other than 0, performing a count-trailing zeroes operation on the returned value to identify a location of a mismatching nucleotide base in the sequence read. In some examples, N=8, 16, 32, or 64 contiguous nucleotide bases.

In some examples, the method further comprises initializing an array representing positions across the reference genome, incrementing an entry of the array representing a position corresponding to a first nucleotide base of the sequence read, and decrementing an entry of the array representing a position corresponding to a last nucleotide base of the sequence read.

In some embodiments described herein, a method for storing support characteristics of positions across a reference genome comprises partitioning the reference genome into a plurality of partitions, each partition comprising contiguous positions of the reference genome; storing support characteristics of positions in a first partition into one or both of a ring buffer and a first temporary storage, wherein the positions are within an active interval that is located fully within the first partition; storing support characteristics of positions in a second partition into one or both of the ring buffer and a second temporary storage, wherein the positions in the second partition is within the active interval that is shifted to be partially located within the first partition and partially located within the second partition; responsive to the position in the first partition no longer being within the active interval, transferring support characteristics of the position in the first partition from one or both of the ring buffer and the first temporary storage to persistent storage; resetting a memory pointer of the first temporary storage; storing support characteristics of positions in a third partition into one or both of the ring buffer and the first temporary storage, wherein the positions in the third partition is within the active interval that is shifted to be partially located within the second partition and partially located within the third partition; responsive to the position in the second partition no longer being within the active interval, transferring support characteristics of the position in the second partition from one or both of the ring buffer and the second temporary storage to persistent storage; and resetting a memory pointer of the second temporary storage.

In some examples, support characteristics of a position comprise one or more of: a number of supporting sequence reads, a number of sequence reads supporting an alternate allele, a number of sequence reads with a first nucleotide base that aligns with the position, a number of sequence reads with a last nucleotide base that aligns with a position immediately preceding the position, an insertion at the position, a deletion at the position, a number of sequence reads with a particular strand orientation supporting an allele at the position, a distribution of estimated fragment lengths for reads supporting an allele at the position, and a set of names of reads supporting an allele at the position.

In some examples, storing support characteristics of the position in the first partition into the ring buffer comprises accessing an array comprising a plurality of entries, wherein a value in an entry in the array represents a support characteristic for the position in the first partition. In some examples, a size of the ring buffer is less than a size of the first temporary storage and the size of the ring buffer is less than a size of the second temporary storage. Further, in some examples, the ring buffer has a size of 1024 elements.

In some examples, storing support characteristics of the position in the second partition into the ring buffer comprises overwriting support characteristics stored in a set of elements of the ring buffer with support characteristics of the position in the second partition. In some examples, the memory pointer of the first temporary storage is reset after support characteristics of all positions within the first partition are transferred to the persistent storage and the memory pointer of the second temporary storage is reset when support characteristics of all positions within the second partition are transferred to persistent storage. In some examples, support characteristics of the position in the first partition that are stored into the ring buffer are bounded support characteristics that are bounded in size and support characteristics of the position in the first partition that are stored into the first temporary storage are unbounded support characteristics that are variable in size.

Further, in some examples, the method includes, while the active interval is partially located within the first partition and partially located within the second partition, further storing support characteristics of additional positions in the first partition into one or both of the ring buffer and the first temporary storage. In some examples, the method includes, while the active interval is partially located within the second partition and partially located within the third partition, further storing support characteristics of additional positions in the second partition into one or both of the ring buffer and the second temporary storage.

In some embodiments described herein, a method for storing support characteristics of positions across a reference genome comprises partitioning the reference genome into a plurality of partitions, each partition comprising contiguous positions of the reference genome; for each sequential pair of adjacent partitions comprising a first partition and a second partition: storing support characteristics of positions in the first partition into persistent storage, the storing comprising iteratively performing the steps of: storing support characteristics of a position in the first partition into a ring buffer and a first temporary storage, wherein the position is within an active interval that is at least partially located within the first partition; and for a completed position in the first partition no longer being within the active interval, transferring support characteristics of the completed position in the first partition from the ring buffer and the first temporary storage to persistent storage; responsive to transferring support characteristics of all positions within the first partition to persistent storage, resetting a memory pointer of the first temporary storage; storing support characteristics of positions in the second partition into persistent storage, the storing comprising iteratively performing the steps of: storing support characteristics of a position in the second partition in the ring buffer and a second temporary storage, wherein the position is within an active interval that is at least partially located within the second partition; and for a completed position in the second partition no longer being within the active interval, transferring support characteristics of the completed position in the second partition from the ring buffer and the second temporary storage to persistent storage; and responsive to transferring support characteristics of all positions within the second partition to persistent storage, resetting a memory pointer of the second temporary storage.

In some embodiments described herein, a non-transitory computer-readable medium stores one or more programs, the one or more programs including instructions which, when executed by an electronic device including a processor, cause the device to perform any of the methods described herein.

In some embodiments described herein, an electronic device comprises one or more processors, a memory, and one or more programs. The one or more programs are stored in the memory and configured to be executed by the one or more processors, and the one or more programs include instructions for performing any of the methods described herein.

BRIEF DESCRIPTION OF THE DRAWINGS

FIG. 3C (SEQ ID NOS: 1 and 2) depicts an example comparison between nucleotide bases of the converted content of the sequence read file and nucleotide bases of the converted reference genome file, in accordance with various embodiments.

FIG. 3D (SEQ ID NOS: 1 and 2) depicts another example comparison in which a mismatched base pair is found between nucleotide bases of the converted content of the sequence read file and nucleotide bases of the converted reference genome file, in accordance with various embodiments.

FIG. 3E (SEQ ID NOS: 1 and 2) depicts yet another example comparison subsequent to the mismatched base pair between nucleotide bases of the converted content of the sequence read file and nucleotide bases of the converted reference genome file, in accordance with various embodiments.

FIG. 4A depicts an example of generating support characteristics for positions across a reference genome and includes an array with multiple initialized entries, in accordance with various embodiments.

FIG. 4B depicts the example array updated to show alignment of a first sequence read to the reference genome, in accordance with various embodiments.

FIG. 4C depicts the example array updated to show alignment of a second sequence read to the reference genome, in accordance with various embodiments.

DETAILED DESCRIPTION

Figure 1:
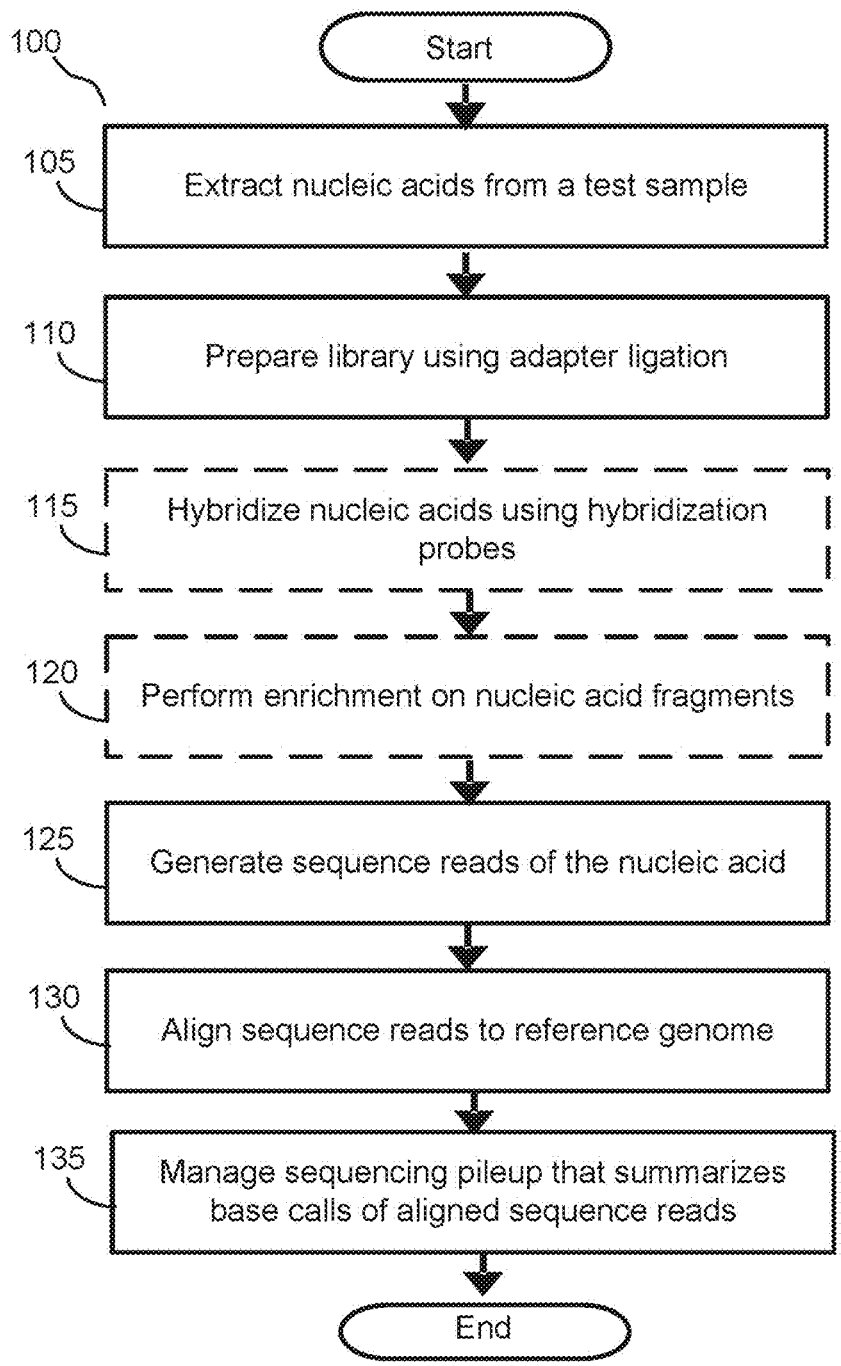
FIG. 1 is an example flow process for managing sequencing pileups, in accordance with various embodiments.

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

The figures use like reference numerals to identify like elements. A letter after a reference numeral, such as "410A," indicates that the text refers specifically to the element having that particular reference numeral. A reference numeral in the text without a following letter, such as "410," refers to any or all of the elements in the figures bearing that reference numeral (e.g. "array 410" in the text refers to reference numerals "array 410A" and/or "array 410B" in the figures).

The subsequent description may express values in binary. Unless otherwise specified, the rightmost bit represents the least significant bit whereas the leftmost bit represents the most significant bit. For example, a value of 2 is expressed as '00000010' whereas a value of 8 is expressed as '00001000.'

Definitions

The term "individual" refers to a human individual.

The term "cell free nucleic acid," "cell free DNA," "cfDNA," "cell free RNA," or "cfRNA" refers to nucleic acid molecules that circulate in an individual's body (e.g., bloodstream) and originate from one or more healthy cells and/or from one or more cancer cells.

The term "genomic nucleic acid," "genomic DNA," or "gDNA" refers to nucleic acid including chromosomal DNA that originates from one or more healthy (e.g., non-tumor) cells. In various embodiments, gDNA can be extracted from a cell derived from a blood cell lineage, such as a white blood cell.

The term "sequence read" refers to nucleotide sequences read from a sample obtained from an individual. Sequence reads can be obtained through various methods known in the art.

The term "reference genome" refers to a nucleic acid sequence database that is a representative example of the genome of a species (e.g., a human).

The term "reference allele" refers to a known allele at a position of a reference genome.

The term "alternative allele" refers to an allele at a position that is different relative to a reference allele at the position.

The term "support characteristics" refers to information that summarizes sequence reads that correspond to a particular position of the reference genome. As used hereafter, "support characteristics" refer to both "unbounded support characteristics" and "bounded support characteristics."

The term "bounded support characteristics" refers to information bounded in size (e.g., a fixed number of nucleotide bases) that summarizes sequence reads that correspond to a particular position of the reference genome. Examples of "bounded support characteristics" of a position include a number of supporting sequence reads, a number of sequence reads supporting an alternate allele, a number of sequence reads with a first nucleotide base that aligns with the position, a number of sequence reads with a last nucleotide base that aligns with a position immediately preceding the position, and a number of sequence reads with a particular strand orientation supporting an allele at the position.

The term "unbounded support characteristics" refers to information that is variable in size (e.g., a variable number of nucleotide bases) that summarizes sequence reads that correspond to a particular position of the reference genome. Examples of "unbounded support characteristics" include an insertion at the position, a deletion at the position, a distribution of estimated fragment lengths for reads supporting an allele at the position, and a set of names of reads supporting an allele at the position.

Methods for Generating Sequence Reads

FIG. 1 is an example flow process 100 for generating a sequencing pileup, in accordance with some embodiments. At step 105, nucleic acids (DNA or RNA) are extracted from a test sample. In various embodiments, the test sample can be a sample selected from the group consisting of blood, plasma, serum, urine, fecal, and saliva samples. Additionally and/or alternatively, in some cases, the test sample is a biological sample that comprises a sample selected from the group consisting of whole blood, a blood fraction, a tissue biopsy, pleural fluid, pericardial fluid, cerebrospinal fluid, and peritoneal fluid. In some embodiments, the test sample can comprise cell-free nucleic acids, examples of which are cell-free DNA and/or cell-free RNA. For example, the test sample can be a cell-free nucleic acid sample taken from a subject's blood. In some embodiments, the cell free nucleic acid sample is extracted from a test sample obtained from a subject known to have cancer (e.g., a cancer patient), or a subject suspected of having cancer. The nucleic acids can be extracted from the test sample through a purification process. In general, any known method in the art can be used for purifying nucleic acids. For example, nucleic acids can be isolated by pelleting and/or precipitating the nucleic acids in a tube.

At step 110, a sequencing library is prepared. During library preparation, adapters, for example, include one or more sequencing oligonucleotides for use in subsequent cluster generation and/or sequencing (e.g., known P5 and P7 sequences used in sequencing by synthesis (SBS) (Illumina, San Diego, CA)) and are ligated to the ends of the nucleic acid molecules through adapter ligation. In some embodiments, unique molecular identifiers (UMIs) are added to the extracted nucleic acids during adapter ligation. The UMIs are short nucleic acid sequences (e.g., 4-10 base pairs) that are added to ends of nucleic acids during adapter ligation. In some embodiments, UMIs are degenerate base pairs that serve as a unique tag that can be used to identify sequence reads obtained from nucleic acids. As described later, the UMIs can be further replicated along with the attached nucleic acids during amplification, which provides a way to identify sequence reads that originate from the same original nucleic acid segment in downstream analysis.

Steps 115 and 120 can be optionally performed. In some examples, steps 115 and 120 are performed when generating sequence reads through a targeted gene panel. As another example, steps 115 and 120 are performed when generating sequence reads through whole exome sequencing. Conversely, in some examples, steps 115 and 120 are not performed when generating sequence reads through whole genome sequencing techniques.

Specifically, at step 115, hybridization probes are used to enrich a sequencing library for a selected set of nucleic acids. Hybridization probes can be designed to target and hybridize with targeted nucleic acid sequences to pull down and enrich targeted nucleic acid molecules that can be informative for the presence or absence of cancer (or disease), cancer status, or a cancer classification (e.g., cancer type or tissue of origin). In accordance with this step, a plurality of hybridization pull down probes can be used for a given target sequence or gene. The probes can range in length from about 40 to about 160 base pairs (bp), from about 60 to about 120 bp, or from about 70 bp to about 100 bp. In some embodiments, the probes cover overlapping portions of the target region or gene. For targeted gene panel sequencing, the hybridization probes are designed to target and pull down nucleic acid molecules that derive from specific gene sequences that are included in the targeted gene panel. For whole exome sequencing, the hybridization probes are designed to target and pull down nucleic acid molecules that derive from exon sequences in a reference genome.

After a hybridization step 115, the hybridized nucleic acid molecules are enriched 120. For example, the hybridized nucleic acid molecules can be captured and amplified using PCR. The target sequences can be enriched to obtain enriched sequences that can be subsequently sequenced. For example, as is well known in the art, a biotin moiety can be added to the 5'-end of the probes (i.e., biotinylated) to facilitate pulling down of target probe-nucleic acids complexes using a streptavidin-coated surface (e.g., streptavidin-coated beads). This improves the sequencing depth of sequence reads.

At step 125, the nucleic acids are sequenced to generate sequence reads. Sequence reads can be acquired by known means in the art. For example, a number of techniques and platforms obtain sequence reads directly from millions of individual nucleic acid (e.g., DNA such as cfDNA or gDNA or RNA such as cfRNA) molecules in parallel.

As an example, sequencing-by-synthesis technologies rely on the detection of fluorescent nucleotides as they are incorporated into a nascent strand of DNA that is complementary to the template being sequenced. In an example method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye.

In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain.

Any suitable sequencing-by-synthesis platform can be used to identify mutations. Sequencing-by-synthesis platforms include the Genome Sequencers from Roche/454 Life Sciences, the GENOME ANALYZER from Illumina/SOLEXA, the SOLID system from Applied BioSystems, and the HELISCOPE system from Helicos Biosciences. Sequencing-by-synthesis platforms have also been described by VisiGen Biotechnologies. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids can be bound to the support by hybridizing the capture sequence to a complementary sequence covalently attached to the support. The capture sequence (also referred to as a universal capture sequence) is a nucleic acid sequence complementary to a sequence attached to a support that can dually serve as a universal primer.

As an alternative to a capture sequence, a member of a coupling pair (e.g., antibody/antigen, receptor/ligand, avidin-biotin pair) can be linked to each molecule to be captured on a surface coated with a respective second member of that coupling pair. Subsequent to the capture, the sequence can be analyzed, for example, by single molecule detection/sequencing, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide can be incorporated and multiple lasers can be utilized for stimulation of incorporated nucleotides.

Massively parallel sequencing or next generation sequencing (NGS) techniques include synthesis technology, pyrosequencing, ion semiconductor technology, single-molecule real-time sequencing, sequencing by ligation, or paired-end sequencing. Examples of massively parallel sequencing platforms are the Illumina HISEQ or MISEQ, ION PERSONAL GENOME MACHINE, the PACBIO RSII sequencer or SEQUEL System, Qiagen's GENEREADER, and the Oxford MINION. Additional similar current massively parallel sequencing technologies can be used, as well as future generations of these technologies.

In various embodiments, a sequence read is comprised of a read pair denoted as $R_1$ and $R_2$. For example, the first read $R_1$ can be sequenced from a first end of a nucleic acid molecule whereas the second read $R_2$ can be sequenced from the second end of the nucleic acid molecule.

At step 130, sequence reads are aligned to a reference genome. The sequence reads can be aligned to a reference genome using known methods in the art to determine alignment position information. The alignment position information can indicate a beginning position and an end position of a region in the reference genome that corresponds to a beginning nucleotide base and end nucleotide base of a given sequence read. Alignment position information can also include sequence read length, which can be determined from the beginning position and end position. A region in the reference genome can be associated with a gene or a segment of a gene. A sequence read file having SAM (sequence alignment map) format or BAM (binary) format can be generated as a result of aligning sequence reads to the reference genome.

At step 135, a sequencing pileup that summarizes base calls of the aligned reads is managed. For example, the sequencing pileup is generated and stored into persistent storage. The sequencing pileup includes support characteristics of positions across the reference genome. The process of determining support characteristics is described in further detail below in relation to FIGS. 2, 3A-3E, and 4A-4C. Generally, the process of determining support characteristics includes three steps: (1) conversion of content in the sequence read file into an internal representation, (2) conversion of the reference genome file into the same internal representation; and (3) comparing nucleotide bases of the converted content in the sequence read file to corresponding nucleotide bases of the converted reference genome file. Furthermore, the steps of storing support characteristics into persistent storage is described in further detail below in relation to FIGS. 5A-5D and 6A-6E.

Determining Support Characteristics of Positions Across the Reference Genome

Figure 2:
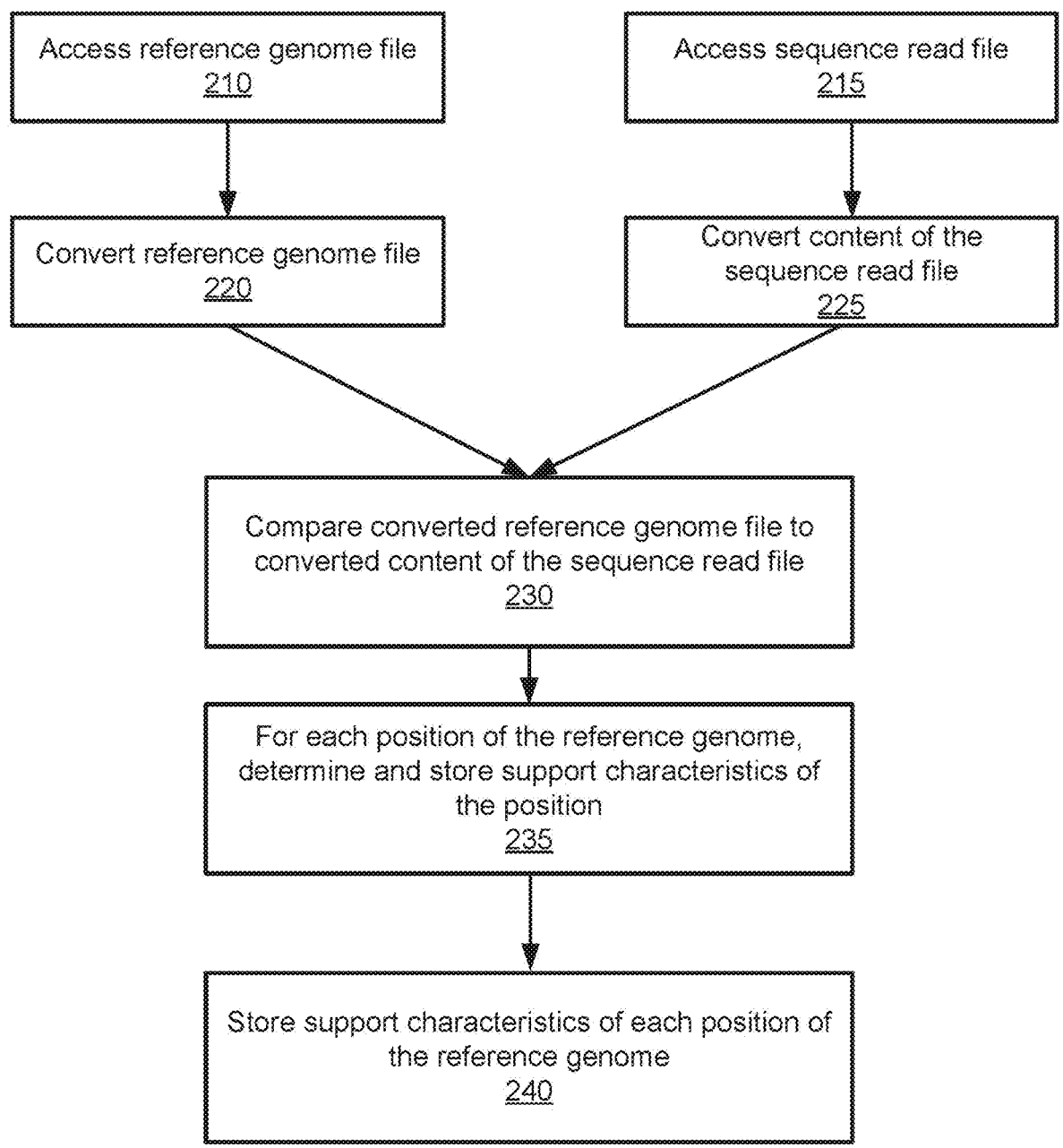
FIG. 2 depicts an overall block diagram for determining and storing support characteristics of positions across a reference genome, in accordance with various embodiments.

FIG. 2 depicts an overall block diagram for determining and storing support characteristics of positions across a reference genome, in accordance with various embodiments. More specifically, FIG. 2 depicts individual steps 210-240 that describe, in further detail, step 135 shown in FIG. 1.

At step 210, a reference genome file is accessed. Generally, the reference genome file can include sequencing data for the genome of a human individual, and more specifically, the genome of a healthy human individual. The sequencing data of the reference genome file is stored in a first format. In various embodiments, the first format of the reference genome file is a FASTA format. The nucleotide bases of the reference genome can be stored as American Standard of Information Interchange (ASCII) encodings. In various embodiments, the adenine nucleotide base is expressed as an ASCII character of 'A' with a byte value of "65" (e.g., binary value of '1000001') or is expressed as an ASCII character of 'a' with a byte value of "97" (e.g., binary value of '1100001'). The cytosine nucleotide base is expressed as an ASCII character of 'C' with a byte value of "67" (e.g., binary value of '1000011') or is expressed as an ASCII character of 'c' with a byte value of "99" (e.g., binary value of '1100011'). The guanine nucleotide base is expressed as an ASCII character of 'G' with a byte value of "71" (e.g., binary value of '1000111') or is expressed as an ASCII character of 'g' with a byte value of "103" (e.g., binary value of '1100111'). The thymine nucleotide base is expressed as an ASCII character of 'T' with a byte value of "84" (e.g., binary value of '1010100') or is expressed as an ASCII character of 't' with a byte value of "116" (e.g., binary value of '1110100'). An unidentified nucleotide base is expressed as an ASCII character of 'N' with a byte value of "78" (e.g., binary value of '1001110') or is expressed as an ASCII character of 'n' with a byte value of "110" (e.g., binary value of '1101110').

At step 215, a sequence read file is accessed. Generally, a sequence read file includes aligned sequencing data (e.g., sequence reads aligned at step 130) generated from a sample obtained from an individual. The sequencing data of the sequence read file is stored in a second format that differs from the first format of the reference genome file. For example, the second format of the sequence read file is in one of a BAM or sequence alignment map (SAM) format.

Here, information of the sequence reads in the sequence read file can be stored across various fields of the sequence read file. The fields of the sequence read file can include one or more of a query template name (QNAME), bitwise flag (FLAG), reference sequence name (RNAME), 1-based leftmost mapping position (POS), mapping quality (MAPA), concise idiosyncratic gapped alignment report (CIGAR) string, reference name of the mate/next read (RNEXT), position of the mate/next read (PNEXT), template length (TLEN), segment sequence (SEQ), and Phred base quality (QUAL).

Referring to the SEQ field, it stores the sequenced nucleotide bases of the sequence read. An adenine nucleotide base is represented by the value of "1," a cytosine nucleotide base is represented by a value of "2,", a guanine nucleotide base is represented by a value of "4," a thymine nucleotide base is represented by a value of "8," and an unidentified nucleotide base is represented by a value of "15." Generally, two adjacent nucleotide bases are stored in a single byte (e.g., 4 bits per nucleotide base). Therefore, M total nucleotide bases of a sequence read can be expressed using M/2 bytes. In various embodiments, the 4 higher order bits of each byte represent a first nucleotide base of a sequence whereas the 4 lower order bits of the byte represent the adjacent second nucleotide base of the sequence. For example, assume that a nucleotide sequence includes adenine at coordinate 0 followed by cytosine at coordinate 1 (e.g. 'AC'). The 4 lower order bits of the byte represents cytosine (e.g., represented in binary as '0010') whereas the 4 higher order bits of the byte represents adenine (e.g., represented in binary as '0001'). Therefore, the byte representation of the 'AC' sequence would be '00010010'. The subsequent byte would store the nucleotide base at coordinate 3 in the four low order bits and the nucleotide base at coordinate 2 in the four high order bits (e.g., [3-2] from the standpoint of a little-endian processor) followed by the further subsequent byte that stores the nucleotide base at coordinate 5 in the four low order bits and the nucleotide base at coordinate 4 in the four high order bits (e.g., [5-4] from the standpoint of a little-endian processor), and so on. Altogether, the organization of nucleotide bases in the SEQ field can be sequentially represented as {X+1, X} {X+3, X+2} {X+5, X+4} . . . where X represents the first coordinate of the sequence.

Referring to the CIGAR string, it represents a sequence of operations and bases that describe the shape of the alignment of the sequence read to the reference genome. Put more generally, the CIGAR string stores alignment information for the corresponding sequence of the sequence read that is stored in the SEQ field. Example CIGAR operations are documented below in Table 1. As an example, if the CIGAR field includes the string of "97M1I9M5S," then the sequence of the sequence read includes 97 nucleotide bases that are aligned to the reference genome, followed by a 1-base insertion, followed by 9 nucleotide bases aligned to the reference genome, followed by 5 ignored soft-clipped nucleotide bases.

TABLE 1

Example CIGAR operations.

| Operation | Description |
| --- | --- |
| "M" | Alignment match |
| "I" | Insertion |
| "D" | Deletion |
| "N" | Skipped region |
| "S" | Soft clipping |
| "H" | Hard clipping |
| "P" | Padding |

At step 220, the reference genome file is converted from the first format to an internal representation. In some embodiments, the internal representation expresses two adjacent nucleotide bases within a single byte (e.g., 4 bits for each nucleotide base). For example, given assigned values for each nucleotide base (e.g., adenine=1, cytosine=2, guanine=4, thymine=8, and an unidentified base=0 or 15), a sequence of adenine-thymine (e.g., 'AT') can be represented in a single byte as '00011000'. In some embodiments, the internal representation expresses a nucleotide base at a particular position using a full byte. Therefore, the nucleotide bases can be expressed in binary values as follows: adenine='00000001', cytosine='00000010', guanine '00000100', thymine='00001000', and an unknown base='00000000' or '00001111'.

In various embodiments, the conversion of the reference genome file can employ a lookup table. In various embodiments, a lookup of up to 16 nucleotide bases, 32 nucleotide bases, or 64 nucleotide bases can be performed in a single clock cycle.

To provide an example, given a line of a reference genome file (e.g., FASTA file) with known length, the first conversion algorithm can be summarized by the following code in the C++ programming language:

In some preferred embodiments, the method uses _mm_shuffle_epi8( ) with an engineered first argument to convert sixteen FASTA values at once. This intrinsic function generates an instruction that is supported by commonly used processors (e.g., major Intel 64-bit processors released since mid-2006, and AMD 64-bit processors since 2011.) In still some embodiments, AVX2 technology can be used. For instance, for even greater efficiency on processors supporting Intel Advanced Vector Extensions 2 (AVX2) or AVX-512 technology, the method uses _mm256_shuffle_epi8( )/_mm512_shuffle_epi8( ) to convert 32-64 FASTA values at once. In some embodiments, partially-uncertain nucleotide bases can also be represented in the FASTA format, such that the present overall method continues to work in the presence of partially-uncertain nucleotide bases.

Figure 3A:
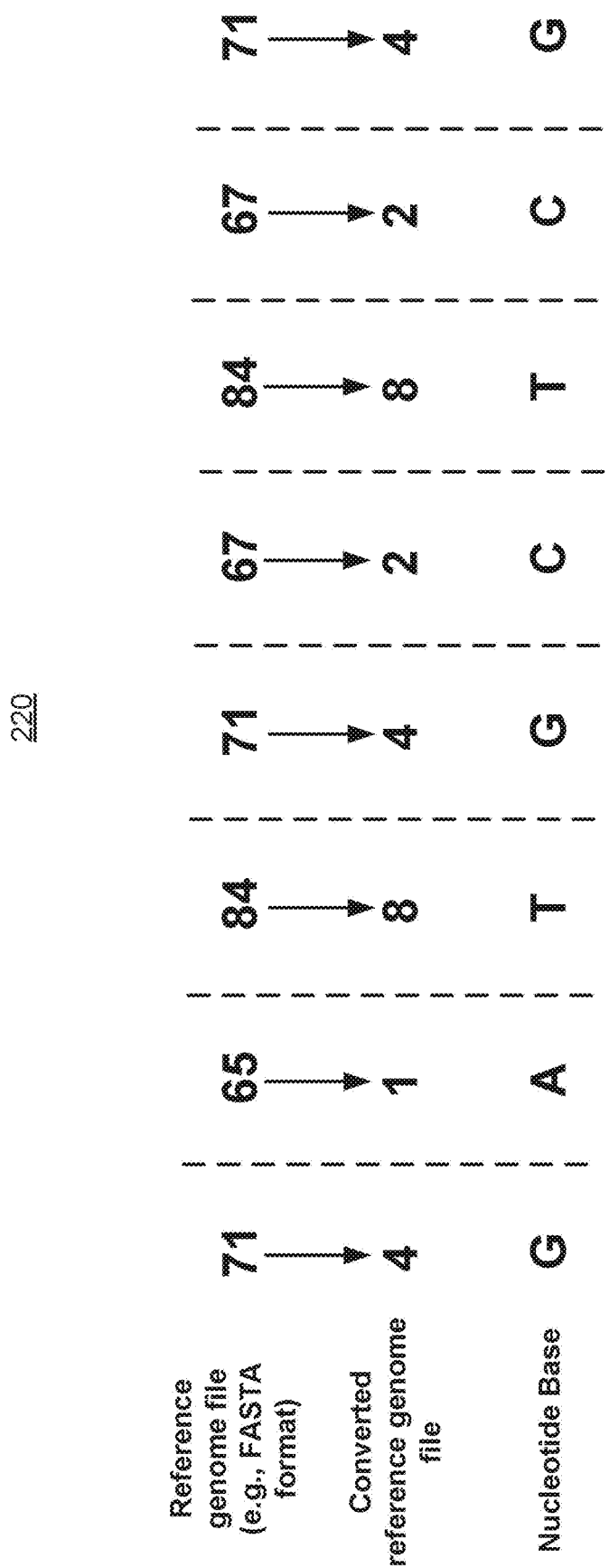
FIG. 3A depicts an example representation of converting the reference genome file into an internal representation, in accordance with various embodiments.

FIG. 3A depicts an example representation of converting the reference genome file into an internal representation, in accordance with various embodiments. Specifically, for a nucleotide sequence of 'GATGCTCG,' the first format of the reference genome file can store byte values of [71] [65] [84] [71] [67] [84] [67] [71] where the brackets (and dotted lines in FIG. 3A) indicate individual bytes. Converting the first format of the reference genome file yields the expression of the nucleotide sequence in byte values of [4] [1] [8] [4] [2] [8] [2] [4].

At step 225, content of the sequence read file is converted from the second format to the internal representation. For example, the content of the sequence read file is the SEQ field that includes the aligned sequence reads. Here, although the second format represents two nucleotide bases in a single byte, which enables efficient data storage, it is more computationally taxing to perform the lookup of the identity of individual nucleotide bases. For example, looking up a single nucleotide base is represented by the following code:

seq_code=(seq[idx>>1]>>(4-4*(idx & 1))) & 15;

which can be computationally slower in comparison to looking up a nucleotide base that is represented by an entire byte. Therefore, converting the sequence read file from the second format to an internal representation that represents each nucleotide base as a single byte provides advantages in processing time.

Generally, the conversion algorithm unpacks and reorders the bits of each byte in order to convert the second format of the sequence read file into the internal representation. More specifically, for a single byte, the four high order bits and the four low order bits are extracted and reordered such that the four higher order bits now precede the four lower order bits. Furthermore, each of the four low order bits and four high order bits are expanded such that the representa-

```
#include <smmintrin.h>
const __m128i fa_to_seq = _mm_setr_epi8(
        0, 1, 0, 2, 8, 0, 0, 4,
        0, 0, 0, 0, 0, 0, 0, 0);
// - line assumed to be a char* pointing to the beginning of a line
// - line_len assumed to be the number of nucleotide bases on the line
// - output assumed to be an unsigned char* pointing past the
//   previous converted line
// - memory assumed to be allocated in a way that lets us safely
//   read/write a few bytes past the end of each array
for (uint32_t idx = 0; idx < line_len; idx += 16) {
        const __m128i fa_text =
            _mm_loadu_si128(reinterpret_cast<const __m128i*>(&(line[idx])));
        const __m128i seq_codes = _mm_shuffle_epi8(fa_to_seq, fa_text);
        _mm_storeu_si128(reinterpret_cast<__m128i*>(&(output[idx])), seq_codes);
}
``` tion of each nucleotide base is now represented by a byte (i.e. four 0 bits can be prepended to each of the four low order bits and the four high order bits). In various embodiments, the steps of extracting, reordering, and expanding the four high order and four low order bits are conducted in less than a single clock cycle per input byte.

As an example, the following conversion algorithm converts a SEQ field of the sequence read file (e.g., BAM file) to a byte-width representation of nucleotide bases:

```
#include <emmintrin.h>
const __m128i m4 = {0x0f0f0f0f0f0f0f0fLLU, 0x0f0f0f0f0f0f0f0fLLU};
// - my_seq_ptr assumed to be a __m128i* pointing to BAM seq data
// - vec_ct assumed to be (l_seq + 31) / 32
// - output assumed to be a __m128i* pointing to the buffer we're writing
//   the converted data to
// - memory assumed to be allocated in a way that lets us safely
//   read/write a few bytes past the end of each array
for (uint32_t vidx = 0; vidx < vec_ct; ++vidx) {
    __m128i cur_seq4 = _mm_loadu_si128(&(my_seq_ptr[vidx]));
    __m128i odd_bases = _mm_and_si128(cur_seq4, m4);
    __m128i even_bases = _mm_and_si128(_mm_srli_epi64(cur_seq4, 4), m4);
    output[2 * vidx] = _mm_unpacklo_epi8(even_bases, odd_bases);
    output[2 * vidx + 1] = _mm_unpackhi_epi8(even_bases, odd_bases);
}
```

This sequence of operations is more than ten times faster than conventional implementations of this function, and it is supported by conventional processors (e.g., Intel and AMD 64-bit processors released since 2003). In some examples, the conversion algorithm can use AVX2 or AVX-512, which can yield an even faster loop.

Figure 3B:
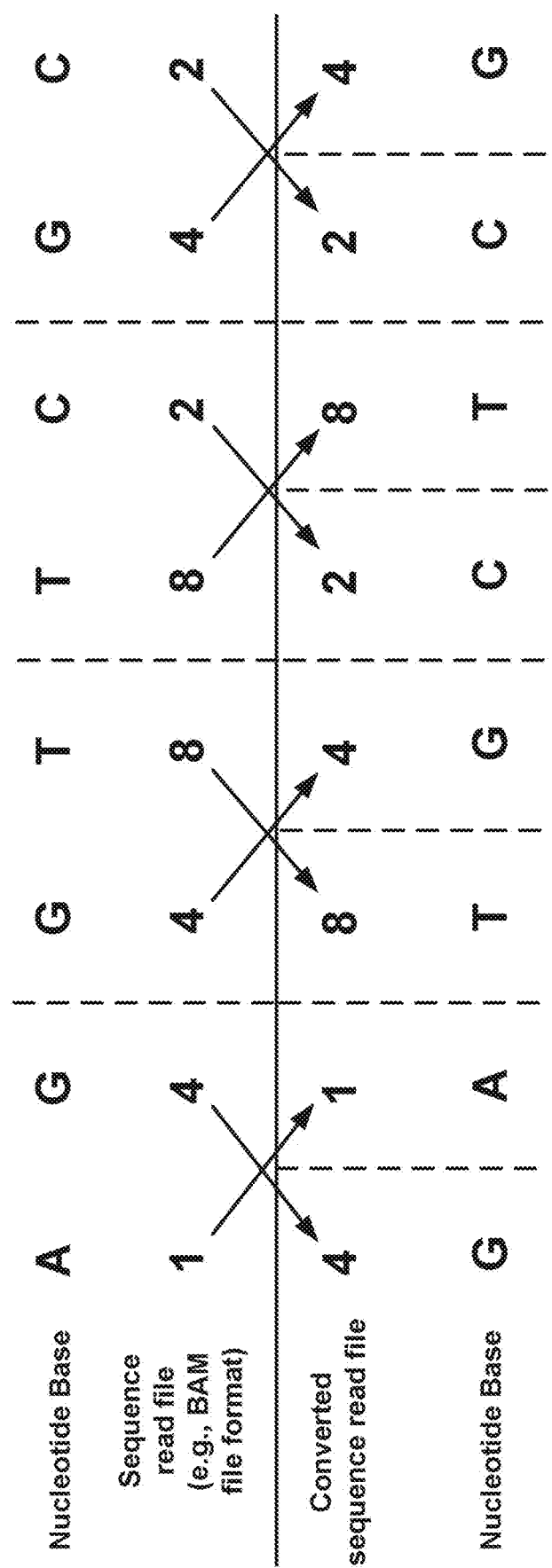
FIG. 3B depicts an example representation of converting content of the sequence read file into an internal representation, in accordance with various embodiments.

FIG. 3B depicts an example representation of converting the content of the sequence read file, such as the SEQ field of the sequence read file, into an internal representation, in accordance with various embodiments. In FIG. 3B, the dotted lines delineate a single byte. In this example, the sequence of nucleotide bases is as follows: 'GATGCTCG.' The SEQ field of the sequence read file for this sequence of nucleotide bases can read [1 4] [4 8] [8 2] [4 2] where each numerical value is represented by four bits and the brackets indicate a full byte. Converting the content of the sequence read file yields the byte-width representation of nucleotide bases. Specifically, the converted content of the sequence read file represents the nucleotide bases as [4] [1] [8] [4] [2] [8] [2] [4].

At step 230, the converted reference genome file is compared to the converted content of the sequence read file. The comparison yields mismatched nucleotide bases at positions across the reference genome, which can be used to determine support characteristics of each position. In other words, the comparison between the converted reference genome file and the converted content of the sequence read file identifies support for reference or alternate alleles at various positions across the reference genome.

The process of comparing the sequences of the converted reference genome file and the converted content of the sequence read file can involve the comparison of N number of bytes of the converted reference genome file to a corresponding N number of bytes of the converted content of the sequence read file. In some embodiments, N=1 byte and therefore, the process involves comparing each nucleotide base (represented by 1 byte) of the converted reference genome file to a corresponding nucleotide base (represented by 1 byte) of the converted content of the sequence read file. In some embodiments, more than 1 byte can be compared at a time (e.g., 8 bytes, 16, bytes, 32 bytes, or 64 bytes). For example, the N number of bytes corresponds to full machine words (e.g., N=8 bytes at a time). By doing so, this comparison process represents an improvement (e.g., faster by at least a factor of five) in comparison to conventional algorithms that compare individual bytes. In another example, N=32 bytes. Here, AVX2 technology can be used to compare 32 bytes a time with _mm256_cmpeq_epi8( ) followed by _mm256_movemask_epi8( ).

In various embodiments, the comparison includes performing a bitwise operation to compare N bytes of the converted reference genome file to a corresponding N bytes of the converted content of the sequence read file. As an example, the bitwise operation is an ANDNOT operation. A bitwise AND-NOT operation can be preferable when partially-uncertain nucleotide bases are present in the sequences. As another example, the bitwise operation is an exclusive-or (XOR) operation. Here, when the XOR operation is conducted, a mismatch between any nucleotide base results in the return of a value other than 0 for the byte corresponding to the nucleotide base. Conversely, matching nucleotide bases return a byte value of 0.

If the bitwise operation yields a value other than 0, an additional operation is performed to determine the precise location of the first mismatching nucleotide base. For example, the additional operation can be a count-trailing-zeroes operation that determines the number of zeroes trailing the first non-zero bit. The number of trailing zeroes indicates the precise bit corresponding to the nucleotide base mismatch. By dividing the number of trailing zeroes by the size of the nucleotide base (e.g., 8 bits) and rounding down to a whole number, the 0-based location of the nucleotide base within the N number of bytes is determined. To provide an example, if N=8 bytes are compared at a time and the count-trailing-zeroes operation returns 42 trailing zeroes, then dividing 42 by the size of the nucleotide base (e.g., 8 bits) and rounding down reveals that, using 0-based indexing, the nucleotide base with position index 5 (i.e. the $6^{th}$ base out of 8) is a mismatch and an alternate allele is present at that location in the sequence read. The nucleotide base of the alternate allele in the allele is additionally determined by querying the value of the byte of the mismatched nucleotide base.

Once the mismatched nucleotide base is identified, the comparison can continue with the subsequent, adjacent nucleotide base. For example, the next N bytes following the mismatched nucleotide base pair in the sequence read file is compared to the corresponding next N bytes in the converted reference genome file. Therefore, the process is repeated until the length of the sequence read is fully compared against the corresponding sequence in the reference genome file.

Example code for performing the comparison between the sequences of the converted reference genome file and the converted content of the sequence read file is shown below:

```
const uintptr_t* my_seq8_ptr =
    reinterpret_cast<const uintptr_t*>(&(seq8[start]));
// - word_ct assumed to be (end - start + kBytesPerWord - 1) / kBytesPerWord
// - my_ref_ptr assumed to be a const uintptr_t* pointing to the first
//   reference genome nucleobase to compare
// - __builtin_ctzl( ) must be replaced with __builtin_ctzll( ) on 64-bit Windows
for (uint32_t widx = 0; widx < word_ct; ++widx) {
    const uintptr_t word_xor = my_seq8_ptr[widx] ^ my_ref_ptr[widx];
    if (word_xor) {
        return start + widx * kBytesPerWord +
            (__builtin_ctzl(word_xor) / CHAR_BIT);
    }
}
return end;
```

In various embodiments, the CIGAR string in the sequence read file is used to guide the comparison between the sequences of the converted reference genome file and the sequences of the converted content of the sequence read file. As described above, the CIGAR string includes operations that identifies insertions, deletions, alignment matches, and others. In some embodiments, sequences within the alignment match (e.g., "M") regions, as identified in the CIGAR string, are compared to corresponding sequences in the converted reference genome file. For example, if the CIGAR string is '97M1I9M5S,' then the 97 nucleotide bases (e.g., indicated by '97M') and the subsequent 9 nucleotide bases (e.g., indicated by '9M') that are aligned to the reference genome are compared to the corresponding sequences of the reference genome. Although the CIGAR string indicates that these stretches of nucleotide bases align with the reference genome, there may be mismatched nucleotide bases within these stretches.

FIGS. 3C, 3D, and 3E depict an example comparison between nucleotide bases of the converted content of the sequence read file and nucleotide bases of the converted reference genome file, in accordance with some embodiments. In this example, N=8 bytes of the converted reference genome file are compared to a corresponding N=8 bytes of the converted content of the sequence read file. Referring first to FIG. 3C, the first 8 bytes of the converted reference genome file, which read 'GATGCTCG,' are compared to the first 8 bytes of the converted content of the sequence read file, which also read 'GATGCTCG.' Here, performing a bitwise comparison between these nucleotide sequences yields 64 bits of zero values. This indicates that the first 8 bytes of the converted reference genome file match with the first 8 bytes of the converted content of the sequence read file. The process need not perform additional operations given that the nucleotide bases are a match.

Referring next to FIG. 3D, the next 8 bytes of the converted reference genome file read 'AAGCTGCA' whereas the next 8 bytes of the converted content of the sequence read file read 'AAGCTNCA.' Importantly, the 6$^{th}$ of the 8 nucleotide bases in the converted content of the sequence read file is an unidentified nucleotide base, which does not match the corresponding 6$^{th}$ of the 8 nucleotide bases in the converted reference genome file. Here, performing a bitwise comparison results in a non-zero value. The bitwise comparison yields 40 zeroes as a result of the first matching 5 nucleotide bases. At the sixth nucleotide base, given that "N" in the converted content of the sequence read file is represented by a binary value of '00001111' and that "G" in the converted reference genome file is represented by a binary value of '00000100,' a bitwise XOR comparison yields a non-zero value of '00001011'. Here, performing a count-trailing-zeroes operation yields a total of forty zeroes. By dividing the forty zeros by the size of each nucleotide base (e.g., 8 bits) and rounding down, the nucleotide base with 0-based position index 5 (i.e. the 6$^{th}$ nucleotide base) is identified as the mismatch.

Referring next to FIG. 3E, the next 8 bytes immediately following the mismatched nucleotide base pair in the sequence read file is compared to the corresponding next 8 bytes in the converted reference genome file. Specifically, the next nucleotide base in the converted content of the sequence read file after the mismatched unidentified (e.g., 'N') nucleotide base serves as the first byte in the next 8 bytes. Any mismatches, if any, in these next 8 bytes are identified and the process continues until the sequence read is fully compared against the corresponding sequence in the reference genome file.

Returning to FIG. 2, at step 235, support characteristics of each position across the reference genome are determined and stored. In various embodiments, support characteristics of various positions can be determined and stored in parallel. For example, one computational thread can determine and store support characteristics for positions in chromosome 1, while another thread simultaneously determines and stores support characteristics for positions in chromosome 2.

Referring to step 235, for each position of the reference genome, the sequence reads that include a nucleotide base that aligns with the position of the reference genome are analyzed to determine the support characteristics for the position. As an example, the support characteristic may refer to a number of sequence reads supporting an alternate allele at the position. Thus, given the mismatched nucleotide bases that are identified for sequence reads at step 230, the total number of sequence reads that include an alternate allele at the position (or total number of sequence reads that include a particular alternate allele at the position) is determined. For example, if the reference genome indicates that an adenine is at a particular position, then the number of sequence reads that include each alternate allele (e.g., cytosine, thymine, guanine, unidentified nucleotide base, insertion, or deletion) can be counted and summated.

In various embodiments, the support characteristics can be determined using an array, where each entry in the array refers to a particular support characteristic at that position. For example, if the particular support characteristic is a number of supporting sequence reads at the position, each entry of an array can document the number of sequence reads that include a nucleotide base that matches the nucleotide base in the reference genome at that position. As another example, each array element can document the difference between the number of supporting reads at a particular position corresponding to the array element in comparison to the number of supporting reads at other positions. In some embodiments, a counter for a position can be incremented for each sequence read with a first nucleotide base that aligns with the position. Additionally and/or alternatively, a counter for a position can be decremented for a number of sequence reads where the last nucleotide base of each sequence read aligns with the immediately preceding position. By doing so, the counter values at each position contains enough information to determine the true supporting-read counts at each position while minimizing the number of counter updates required.

In some embodiments, multiple different arrays are initialized, where each array is specific for one or more support characteristics. For example, a first array can document the number of reference-base supporting sequence reads at positions across the genome, arrays #2-4 can document the number of sequence reads that support each possible single-base alternate allele at the position, and so on.

Reference is now made to FIGS. 4A-4C, which depict an example of generating support characteristics for positions across a reference genome, in accordance with various embodiments. Although each of FIGS. 4A-4C depict a single array 410, in some embodiments, there can be multiple arrays that each document one or more support characteristics for positions across the reference genome. Specifically, the array 410 shown in FIGS. 4A-4C documents the difference between the number of supporting reads at a position in comparison to the number of supporting reads at other positions; from this, the number of supporting reads at each position can be quickly reported.

Referring first to FIG. 4A, an array 410 with multiple entries is initialized. Upon initialization, each entry can include a value of 0. Additionally, each entry can correspond to a position in the reference genome. Referring to FIG. 4B, a first sequence read 420A is analyzed. As shown in FIG. 4B, the sequence reads 420A and 420B are 150 nucleotide bases in length. In some embodiments, the length of the sequence read can vary within a known range (e.g., 1 to 160 nucleotide bases). The first sequence read 420A is aligned to the reference genome at positions [5, 155). Thus, the entry in the array 410 corresponding to position 5 is incremented by a value of one, thereby indicating that the first nucleotide base of the first sequence read 420A aligns with position 5. Additionally, the entry in the array 410 corresponding to position 155 is decremented by a value of one, thereby indicating that the last nucleotide base of the first sequence read 420A aligns with position 154. Incrementing only the entry corresponding to the first nucleotide base and decrementing only the entry corresponding to the last nucleotide base represents an improvement in comparison to conventional pileup algorithms that typically increment over every position of the reference genome that the sequence read aligns to.

Referring next to FIG. 4C, a second sequence read 420B is analyzed. Here, the second sequence read 420B is aligned to the reference genome at positions [7, 157). Therefore, the entry corresponding to position 7 is incremented by a value of one and the entry corresponding to position 157 is decremented by a value of one. As subsequent sequence reads are analyzed, entries of the array 410 can be further incremented or decremented. Once the sequence reads are analyzed, the resulting array 410 represents the support characteristics that can be subsequently stored.

Storing Support Characteristics Using an Improved Memory Allocation Process

FIGS. 5A-D depict a flow process of an improved memory allocation process for storing support characteristics, in accordance with some embodiments. The memory allocation process will additionally be described in reference to FIGS. 6A-6E, each of which depict the storage of support characteristics into the persistent storage 650 using a ring buffer 615 and multiple temporary storages 625 and 630, in accordance with an embodiment. Given that the support characteristics of each position can, in some cases, be variable in length (e.g., insertions and deletions vary in length), the amount of memory that needs to be dedicated to manage support characteristics of differing positions is unbounded. Thus, dynamic allocation using the temporary storages 625 and 630 enables the management of the unbounded information represented by supporting characteristics of differing positions. Generally, the first temporary storage 625 and second temporary storage 630 can each represent a portion of a computer's random access memory (RAM). Conversely, the persistent storage 650 can represent a computer's hard drive, such as a hard disk drive (HDD) or a solid state drive (SSD).

Specifically, FIGS. 5A-D describe the step of determining and storing support characteristics (e.g., step 240 shown in FIG. 2) in further detail. Here, this process consumes fewer computational resources that are dedicated to allocation and freeing operations. Dynamic memory allocation and freeing operations are frequently responsible for a significant fraction of a computer program's execution time. Therefore, in comparison to conventional systems, the memory allocation process described herein represents a significant improvement to a computer through the reduction of a computer program's execution time.

The memory allocation process shown in FIGS. 5A-5D is a looping process for storing support characteristics of positions across different partitions of the reference genome. Each partition is composed of a number of contiguous positions of the reference genome. In various embodiments, each partition includes 1024 contiguous positions. Therefore, a first partition can include genomic positions 0-1023, a second partition can include genomic positions 1024-2047, and so on. In some embodiments, each partition can contain fewer or additional contiguous positions (e.g., 512, 2048, 4096, or 8192 contiguous positions).

Specifically, for each process loop (e.g., steps of FIGS. 5A-5D), the memory allocation process stores support characteristics of positions across two adjacent partitions. Therefore, by repeating the process loop (e.g., steps shown in FIGS. 5A-5D), support characteristics of positions across sequential pairs of partitions of the reference genome can be stored. For example, for a first process loop, support characteristics of positions in partitions 1 and 2 are stored. For a second process, support characteristics of positions in the next sequential pair of partitions (e.g., partitions 3 and 4) are stored.

Additionally, each of FIGS. 5A-5D further depicts an iterative process for storing support characteristics for positions within a particular partition while using an active interval that is shifted along the reference genome for each iteration. In general, the active interval for a position refers to a length along the reference genome such that sequence reads that align with the reference genome within the active interval influence the support characteristics for the position. In other words, sequence reads that align with the reference genome within the active interval can be analyzed to determine the support characteristics for the position. In various embodiments, the size of the active interval is dependent on a fixed-length sliding window with length W. For a position located at coordinate X, the active interval for the position can be denoted as:

Active Interval: [X−W,X+W]

In various embodiments, the length W of the fixed-length sliding window can be based on the maximum sequence read length. For example, the length W of the fixed-length sliding window can be 255 nucleotide bases in length, to be sufficient for length-150 reads containing up to 105 deleted reference bases in their alignment. In some embodiments, the active interval can be defined for a coordinate X using two differently sized windows (e.g., with length $W_1$ and $W_2$). For example, the active interval can be denoted as:

Active Interval: [X−$W_1$,X+$W_2$]

The length $W_1$ can be dependent on a maximum DNA fragment length of interest and the length $W_2$ can be dependent on a maximum sequence read length.

Generally, at any given time, support characteristics for positions across the active interval are determined and stored by analyzing the sequence reads within the active interval. Although the subsequent description may refer to determining and storing support characteristics for an individual position, it is to be understood that support characteristics for other positions across the active interval can be additionally performed.

Figure 5A:
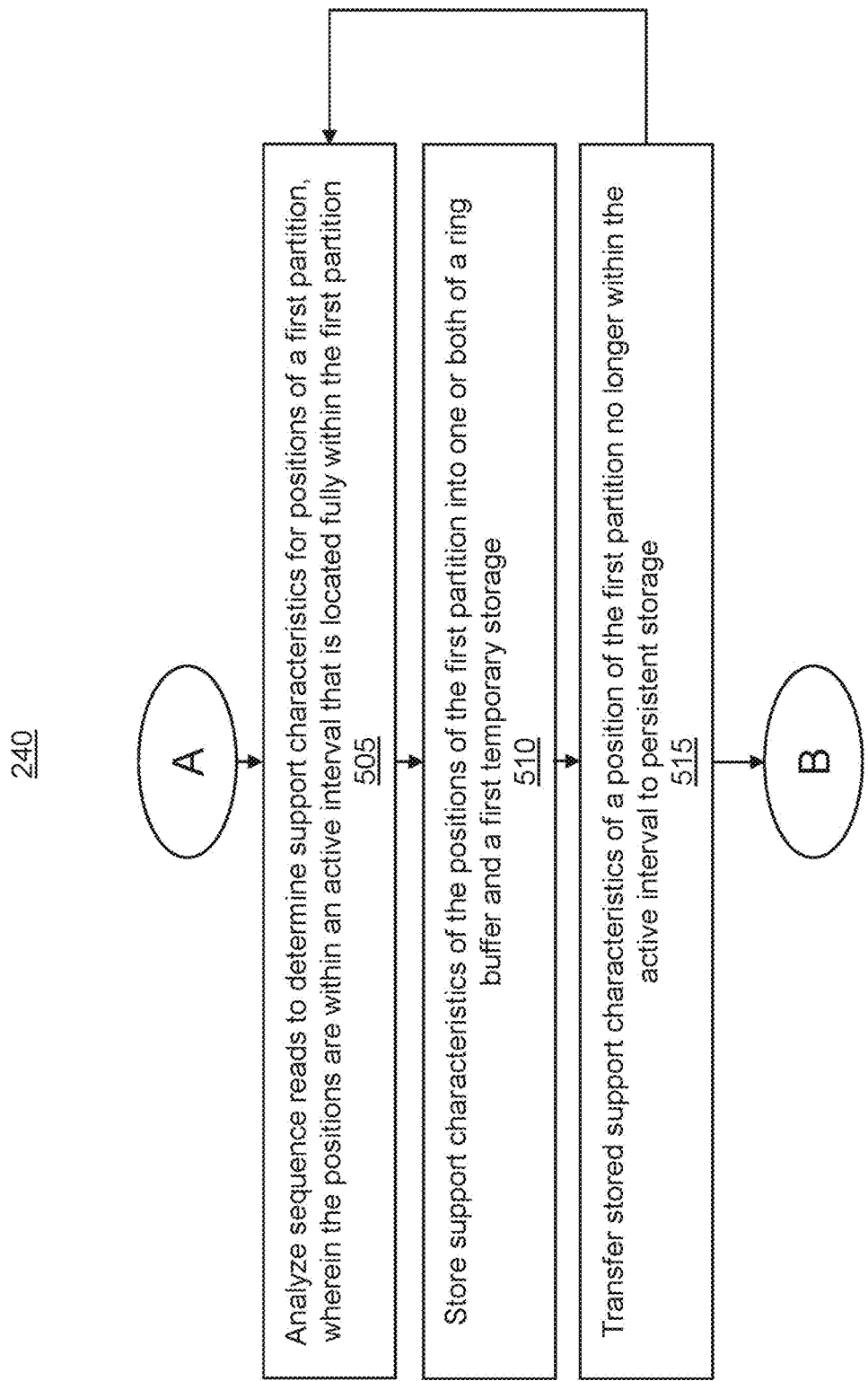
FIG. 5A depicts a flow diagram of an improved memory allocation process for storing support characteristics, such as an iterative process of storing support characteristics of positions in a first partition while an active interval is fully located within the first partition, in accordance with various embodiments.
Figure 5B:
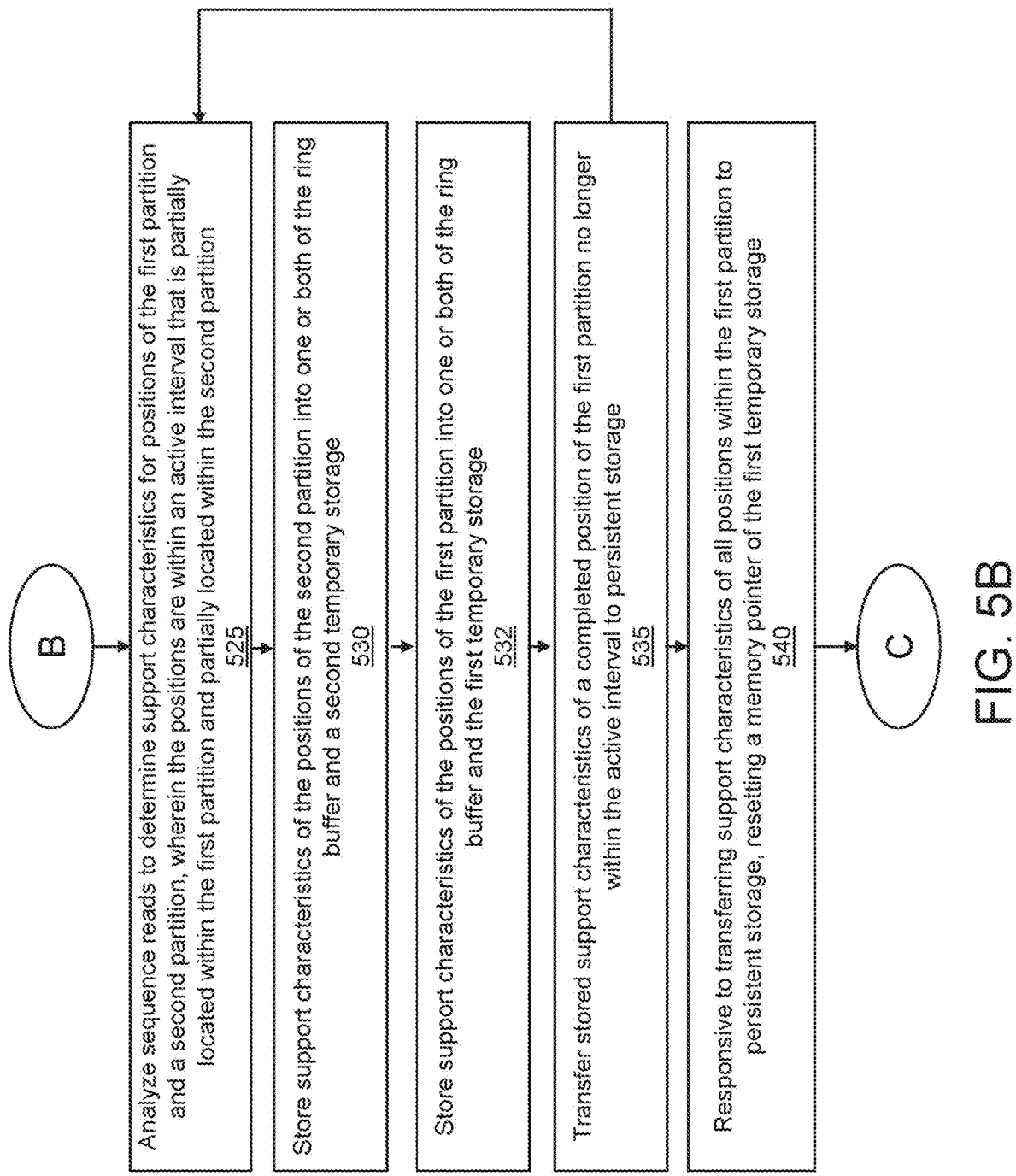
FIG. 5B depicts an iterative process of storing support characteristics of positions of the first partition while an active interval is partially located within the first partition and partially located within a second partition, in accordance with various embodiments.
Figure 5C:
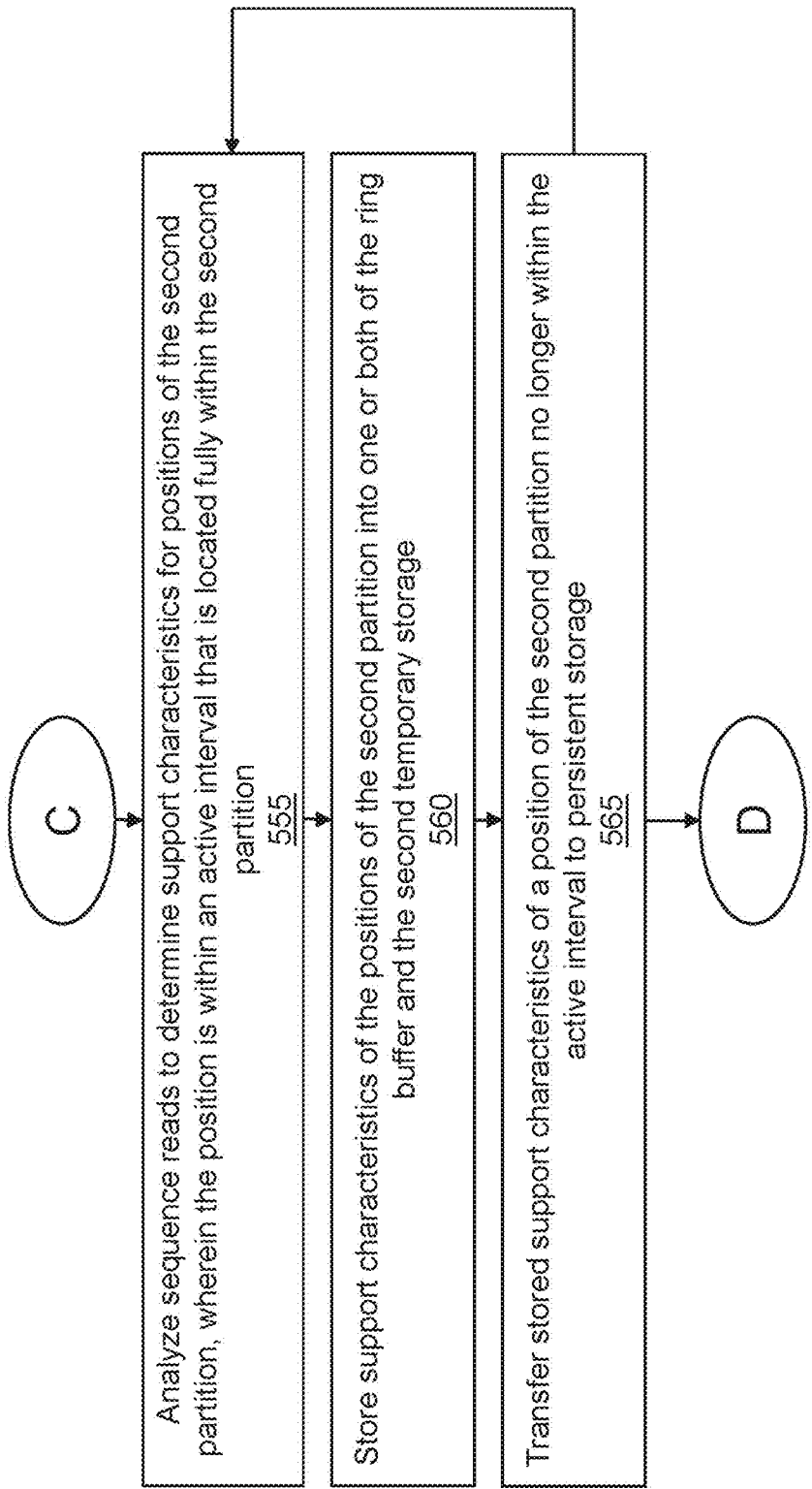
FIG. 5C depicts an iterative process for storing support characteristics of positions in the second partition while an active interval has been further shifted to be fully located within the second partition, in accordance with various embodiments.
Figure 5D:
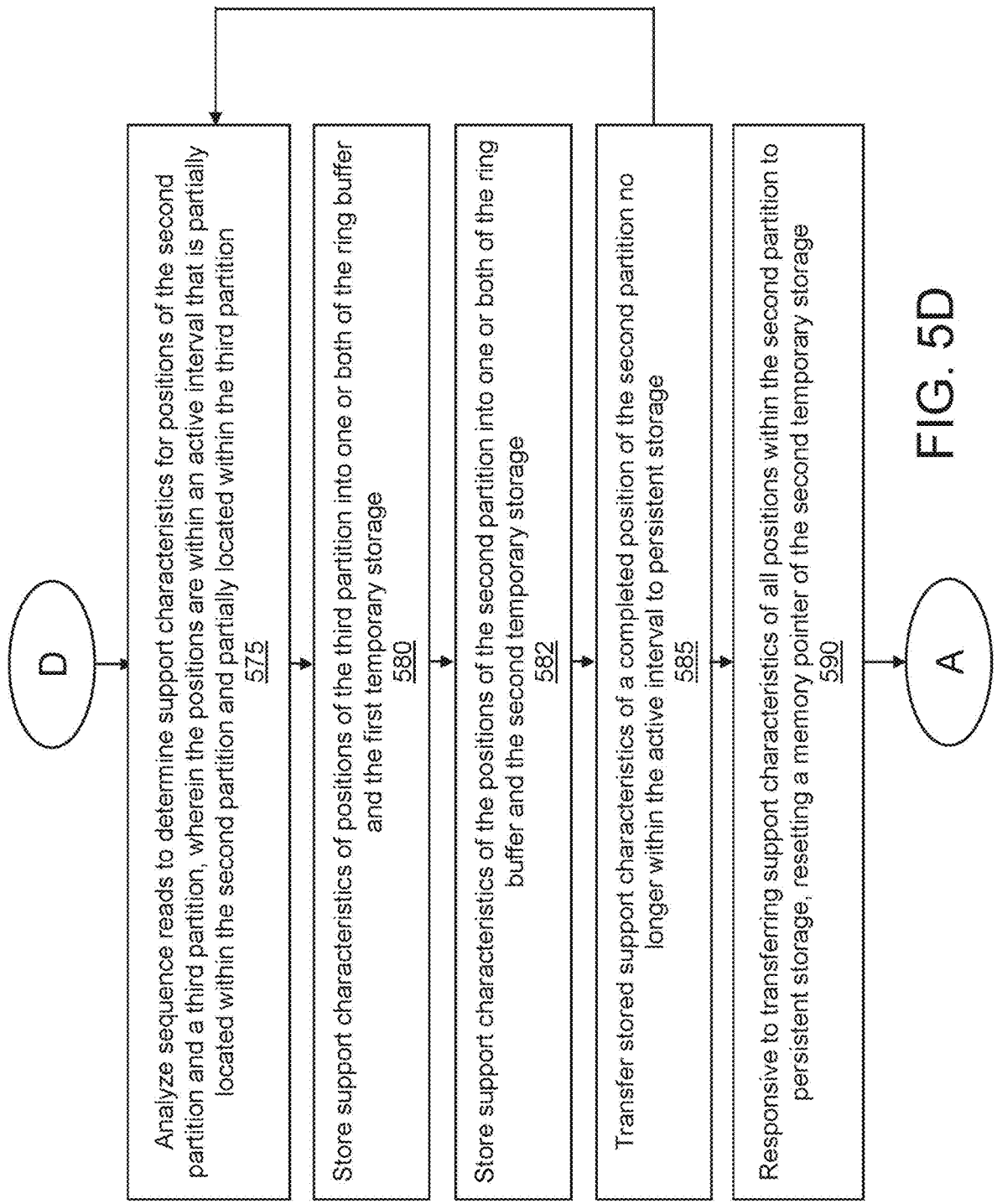
FIG. 5D depicts an iterative process for storing support characteristics of positions in the second partition while the active interval is shifted to be partially located within the second partition and partially located within a third partition, in accordance with various embodiments.

Referring to FIG. 5A, it depicts an iterative process (e.g., steps 505-515) of storing support characteristics of positions in a first partition while an active interval is fully located within the first partition. FIG. 5B depicts an iterative process (e.g., steps 525-535) for storing support characteristics of positions in the first partition while the active interval has been shifted to be partially located within the first partition and partially located within a second partition. FIG. 5C depicts an iterative process (e.g., steps 555-565) for storing support characteristics of positions in the second partition while an active interval has been further shifted to be fully located within the second partition. FIG. 5D depicts an iterative process (e.g., steps 575-585) for storing support characteristics of positions in the second partition while the active interval is shifted to be partially located within the second partition and partially located within a third partition.

For each of the iterative processes in each of FIGS. 5A-5D, at each iteration, the active interval is shifted along the reference genome by one or more genomic positions. For example, for a first iteration, the active interval can include positions 1-301. Next, for a second iteration, the active interval can include positions 2-302.

Beginning at step 505 of FIG. 5A, sequence reads are analyzed to determine support characteristics for positions within the active interval that is located within a first partition. Determining support characteristics for positions is described above in relation to FIGS. 4A-4C.

At step 510, the support characteristics of positions of the first partition are stored into one or both of a ring buffer and a first temporary storage. Generally, support characteristics that are bounded in size, hereafter referred to as bounded support characteristics (e.g., an alternate single nucleotide polymorphism (SNP) supporting read count is a fixed 4 bytes in size, if 32-bit integers are used, and there are only 3 possible SNPs at each position), are stored into the ring buffer whereas support characteristics that are variable in size, hereafter referred to as unbounded support characteristics (e.g., an insertion or deletion at a position can be variable nucleotide bases in length) are stored into the first temporary storage. Additionally, unbounded support characteristics that are stored into the first temporary storage have a corresponding stack indicator stored into the ring buffer, where the corresponding stack indicator identifies the location in the first temporary storage that the unbounded support characteristics are located at. Maintaining a stack indicator enables the retrieval of the unbounded support characteristics from the first temporary storage at a subsequent time (e.g., when transferring the unbounded support characteristics from the first temporary storage to persistent storage).

As described above, support characteristics of each position can be stored across multiple arrays, where each array is specific for a particular support characteristic. Therefore, the process of storing support characteristics of a position in the ring buffer involves accessing each of the one or more arrays and identifying an entry in each array that corresponds to the position. For each array, the value in the identified entry of each array is extracted. Thus, the different types of support characteristics of the position across the arrays can be stored into the elements of the ring buffer or into the first temporary storage.

In various embodiments, the size of the ring buffer is dependent on the length of the fixed-length sliding window that defines the active interval. At any given time, there are 2 W+1 total genomic positions within an active interval. Therefore, to manage the support characteristics of the 2 W+1 genomic positions within the active interval at one time, the ring buffer can be configured with a size of 2 W+2 elements. In particular embodiments, the ring buffer can include 1024 elements. In other embodiments, the ring buffer includes fewer (e.g., 512) or additional (e.g., 2048, 4096, 8192, or more) elements. Generally, the size of the ring buffer is minimized such that only a subset of positions in the partition can be stored in the ring buffer at any given time.

The elements of the ring buffer can be fully occupied and therefore, storing bounded support characteristics of a position often involves overwriting prior data in the elements of the ring buffer. The prior data can be bounded support characteristics of a prior position. Generally, the prior data in the ring buffer that is to be overwritten are bounded support characteristics of a lowest position in the reference genome in comparison to positions corresponding to other bounded support characteristics in the ring buffer. For example, if bounded support characteristics of position 301 are to be written to a ring buffer that holds bounded support characteristics of positions 1-300, then the bounded support characteristics of position 1 are first overwritten in order to allow bounded support characteristics of position 301 to be stored in the ring buffer.

Referring to the storage of unbounded support characteristics of a position of the first partition into the first temporary storage, the unbounded support characteristics are stored at a location (e.g., address) indicated by a memory pointer of the first temporary storage. After storing unbounded support characteristics of a position at the location of the first temporary storage, the memory pointer of the first temporary storage is updated to the next still-unused memory byte or word. Therefore, subsequent information that is stored in the first temporary storage can be appropriately stored at the next available address indicated by the memory pointer. If unbounded support characteristics of multiple positions are to be stored in the first temporary storage, the unbounded support characteristics can be stored through an iterative process. For example, the unbounded support characteristics of a first position can be stored at the location indicated by the memory pointer of the first temporary storage, the memory pointer is updated, and the process can be iterated for unbounded support characteristics of subsequent positions.

At step 515, support characteristics of a position that is no longer within the active interval are transferred to persistent storage. Such a position that is no longer within the active interval is hereafter referred to as a "completed position." Support characteristics of a completed position can be transferred from one or both of the ring buffer and the first temporary storage to the persistent storage. To provide an example, the ring buffer and the first temporary storage can each store support characteristics for positions 1-302 whereas the current active interval may have been shifted by a genomic position to now include positions 2-303. Therefore, the support characteristics for completed position 1 that is stored in the ring buffer and/or the first temporary storage are transferred to the persistent storage as completed position 1 is no longer within the current active interval.

Next, step 505 is repeated. Here, the active interval, which still remains fully within the first partition, is now shifted by a genomic position in comparison to the prior iteration. For example, in the previous iteration, the active interval can include genomic positions 2-303. Here, when repeating step 505, the active interval is now shifted by a genomic position to include genomic positions 3-304. Thus, sequence reads that align with the reference genome within the shifted active interval are analyzed to determine support characteristics for positions within the shifted active interval (e.g., new position 304 included in the active interval). Steps 510 and 515 can be repeated in this iteration such that support characteristics of completed position 2, which is no longer in the active interval, are transferred to persistent storage. Steps 505-515 are further iterated until the active interval enters into a subsequent partition (e.g., second partition located subsequent and adjacent to the first partition).

Referring now to FIG. 5B, it depicts an iterative process of storing support characteristics of positions of the first partition while an active interval is partially located within the first partition and partially located within a second partition. At step 525, sequence reads are analyzed to determine support characteristics of positions in the first partition and positions in the second partition. Here, positions in the first partition and positions in the second partition are located within the active interval.

At step 530, support characteristics of positions of the second partition are stored into one or both of the ring buffer and the second temporary storage. The process of storing support characteristics of the position in the second partition into the ring buffer and/or the second temporary storage is similar to the process of storing support characteristics of the position of the first partition into the ring buffer and/or the first temporary storage, as described in step 510. For example, bounded support characteristics of the position in the second partition are stored into the ring buffer whereas unbounded support characteristics of the position in the second partition are stored into the second temporary storage. Additionally, unbounded support characteristics that are stored into the second temporary storage have a corresponding stack indicator stored into the ring buffer, where the corresponding stack indicator identifies the location in the second temporary storage that the unbounded support characteristics are located at.

Additionally, support characteristics of other positions in the active interval that are within the first partition can continue to be stored in the ring buffer and the first temporary storage. Specifically, at step 532, support characteristics of positions of the first partition (e.g., positions of the first partition that are within the active interval) are stored into one or both of the ring buffer and the first temporary storage.

At step 535, support characteristics of a completed position of the first partition no longer within the active interval are transferred to persistent storage from one or both of the ring buffer and the first temporary storage.

Steps 525-535 are iteratively performed to continue storing support characteristics of positions within the first partition into the persistent storage. At step 540, when the active interval fully exits the first partition (e.g., the active interval is now only in the second partition), then the support characteristics of all positions in the first partition have been transferred to persistent storage. Therefore, the information in the first temporary storage is stale and no longer needed. The memory pointer for the first temporary storage is reset; in combination with standard ring buffer updates, this effectively erases all information in the first temporary storage, without the complicated and relatively slow bookkeeping usually needed to manage an arbitrary number of mixed-order variable-size records.

Referring now to FIG. 5C, it depicts an iterative process of storing support characteristics of positions while an active interval is fully located within the second partition. At step 555, sequence reads are analyzed to determine support characteristics of positions in the second partition, wherein the positions are located within the active interval. At step 560, support characteristics of positions of the second partition are stored into one or both of the ring buffer and the second temporary storage. At step 565, support characteristics of a completed position of the second partition no longer within the active interval are transferred to persistent storage.

Steps 555-565 are iteratively performed to continue storing support characteristics of positions within the second partition into the persistent storage. These steps are repeated until the active interval enters into a subsequent partition (e.g., third partition) adjacent to the second partition.

Referring now to FIG. 5D, it depicts an iterative process of storing support characteristics of positions within the second partition while an active interval is partially located within the second partition and partially located within the third partition. At step 575, sequence reads are analyzed to determine support characteristics of positions in the second and third partitions. At step 580, support characteristics of the positions of the third partition are stored into one or both of the ring buffer and the first temporary storage. Here, the process of storing support characteristics of the position in the third partition into the ring buffer and/or the first temporary storage is similar to the process of storing support characteristics of the position of the first partition into the ring buffer and/or the first temporary storage, as described in step 510. As described above, the first temporary storage was cleared and therefore, while the second temporary storage is utilized to manage unbounded support characteristics of positions in the second partition, the first temporary storage can now be re-used to store unbounded support characteristics of positions in the third partition.

Additionally, support characteristics of other positions in the active interval that are within the second partition can continue to be stored in the ring buffer and the first temporary storage. Specifically, at step 582, support characteristics of positions of the second partition (e.g., positions of the second partition that are within the active interval) are stored into one or both of the ring buffer and the second temporary storage.

At step 585, support characteristics of a completed position of the second partition no longer within the active interval are transferred to persistent storage.

Steps 575-585 are iteratively performed to continue storing support characteristics of positions within the second partition into the persistent storage. At step 590, when the active interval fully exits the second partition (e.g., the active interval is now only in the third partition), then the support characteristics of all positions in the second partition have been transferred to persistent storage. Therefore, the information in the second temporary storage is stale and no longer needed. The memory pointer of the second temporary storage is reset and the information in the second temporary storage is erased.

Following step 590, the memory allocation process can continue by restarting at step 505 as the active interval is now fully located within the third partition. Therefore, the process (e.g., steps 505-590) shown in FIGS. 5A-5D can be repeated to store support characteristics of positions across the next two partitions (e.g., third and fourth partition). The steps can be further iterated to store support characteristics of positions across all partitions of the reference genome.

Figure 6A:
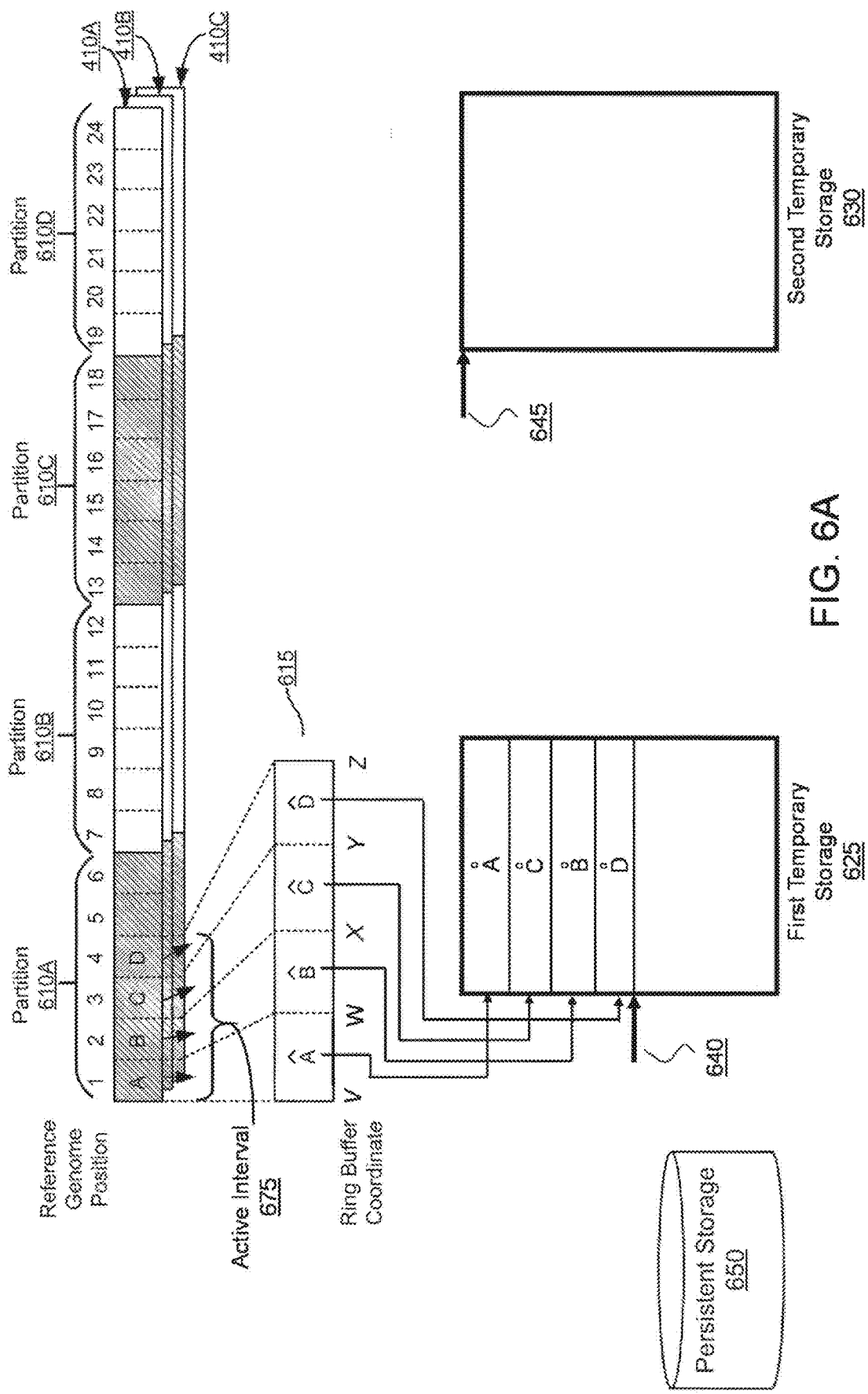
FIG. 6A depicts the storage of support characteristics into persistent storage using a ring buffer and temporary storages an active interval is fully located within a first partition, in accordance with various embodiments.

To provide a visual example of the memory allocation process, reference is made to FIGS. 6A-6E. In FIG. 6A, the reference genome is partitioned into multiple partitions 610. For ease of explanation, each partition 610 shown in FIG. 6A includes 6 positions; however, in various embodiments, each partition 610 can include upwards of 1024 or more positions. As shown in FIG. 6A, a first partition 610A includes positions 1-6 of the reference genome, a second partition 610B includes positions 7-12 of the reference genome, a third partition 610C includes positions 13-18, and a fourth partition 610D includes positions 19-24. Support characteristics of various positions across the reference genome can be represented in a first array 410A, a second array 410B, and a third array 410C where each array 410 represents a different support characteristic.

In this example, the first entry of the first array 410A corresponds to position 1 of the reference genome, the second entry of the first array 410A corresponds to position 2 of the reference genome, the third entry of the first array 410A corresponds to position 3 of the reference genome, and the fourth entry of the first array 410A corresponds to position 4 of the reference genome.

In this scenario, the active interval 675 is fully located within the partition 610A. For ease of explanation, the active interval 675 is denoted in FIG. 6A as corresponding to positions 1-4. In general, the active interval 675 can include significantly more genomic positions (e.g., 301 or more genomic positions). As shown in FIG. 6A, one type of support characteristics for the genomic positions within the active interval 675 (e.g., positions 1-4) are represented as the values of "A," "B," "C," and "D." Although not explicitly shown, the first entry of the second array 410B and the first entry of the third array 410B may each represent another value reflecting other support characteristics of the first position. The second entry of the second array 410B and the second entry of the third array 410B can each represent a value reflecting other support characteristics of the second position, and so on.

The ring buffer 615 shown in FIG. 6A includes coordinates that are denoted as V, W, X, Y, and Z. Here, bounded support characteristics of positions 1-4 are stored in the ring buffer 615. Specifically, elements between coordinates V and W of the ring buffer 615 store bounded support characteristics of position 1, denoted as A, that are aggregated across the first entry of each of arrays 410A, 410B, and 410C. Additionally, elements between coordinates W and X of the ring buffer 615 store bounded support characteristics of position 2, denoted as $\hat{B}$, elements between coordinates X and Y of the ring buffer 615 store bounded support characteristics of position 3, denoted as $\hat{C}$, and elements between coordinates Y and Z of the ring buffer 615 store bounded support characteristics of position 4, denoted as $\hat{D}$. Additionally, the ring buffer stores, for each of positions 1-4, stack indicators that each identifies a corresponding location in the first temporary storage that unbounded support characteristics for each position are stored. As shown in FIG. 6A, the stack indicators in the ring buffer 615 point to particular locations in the first temporary storage where the corresponding unbounded support characteristics of positions 1-4, denoted as $A^°$, $B^°$, $C^°$, and $D^°$, respectively, are stored in the first temporary storage.

The first temporary storage 625 includes a memory pointer 640 that, upon storing the unbounded support characteristics of positions 1-4, is updated to the next available allocation available in the first temporary storage 625. The unbounded support characteristics of positions 1-4 can be stored in an out-of-order manner. In this example, assume that a first sequence read differs from the reference genome at positions 1 and 3 and a second sequence read differs from the reference genome at positions 2 and 4. Thus, the analysis of the first sequence read yields unbounded support characteristics of positions 1 and 3 (denoted as $A^°$ and $C^°$) that are first stored into the first temporary storage 625. Next, the analysis of the second sequence read yields unbounded support characteristics of positions 2 and 4 (denoted as $B^°$ and $D^°$) that are stored into subsequent locations of the first temporary storage 625.

Figure 6B:
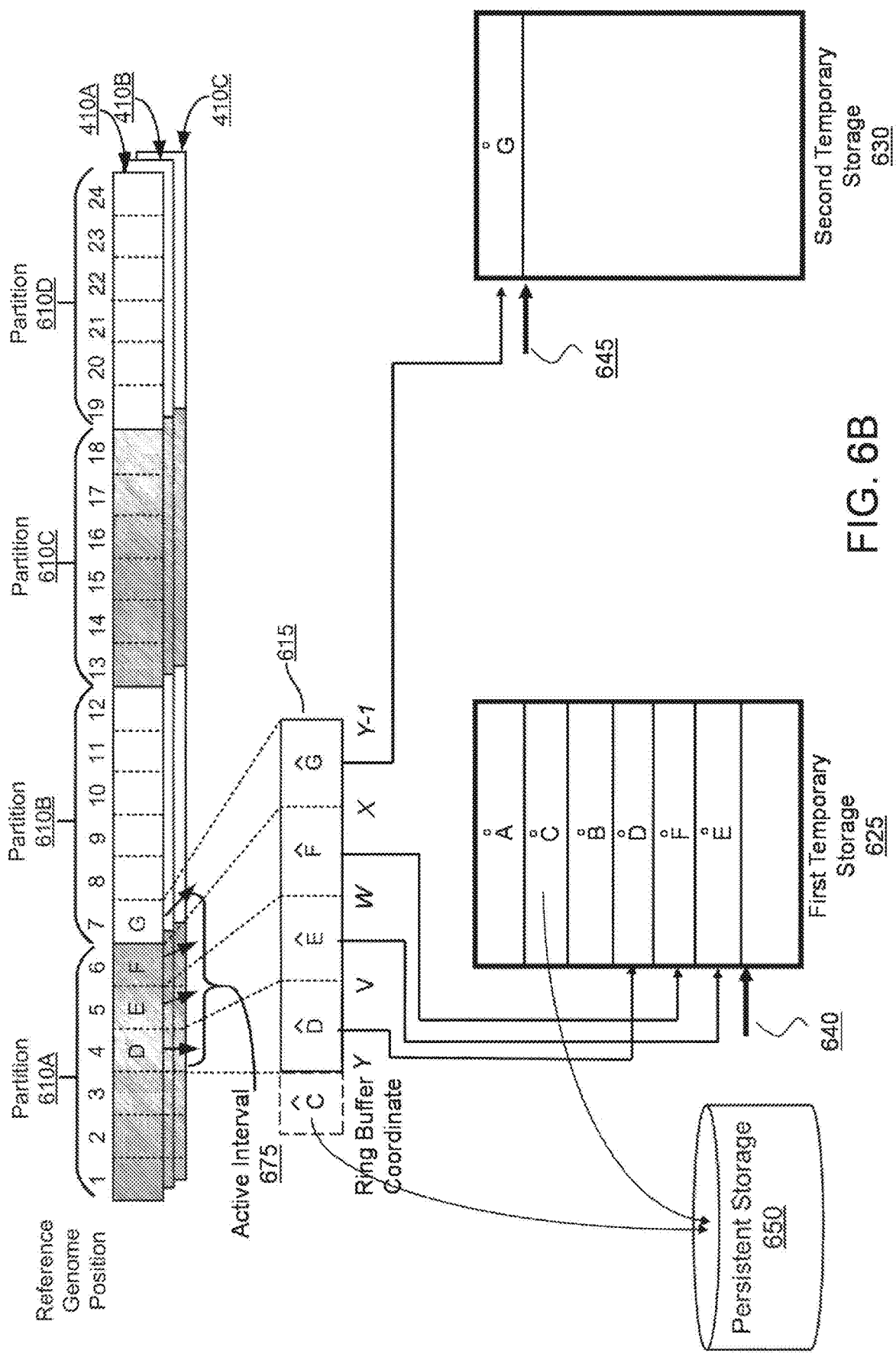
FIG. 6B depicts the storage of support characteristics into persistent storage when the active interval is shifted to be located within both the first partition and a second partition, in accordance with various embodiments.

Referring now to FIG. 6B, the active interval is now shifted to include positions 4-7, where positions 4-6 are of partition 610A and where position 7 is from partition 610B. In other words, the active interval now spans across multiple partitions 610. Bounded and unbounded support characteristics of positions 5 and 6 are determined. The bounded support characteristics of positions 5, 6, and 7 (denoted as $\hat{E}$, $\hat{F}$, and $\hat{G}$ respectively) are stored into the ring buffer 615, whereas unbounded support characteristics of positions 5, 6, and 7 (denoted as $E^°$, $F^°$, and $G^°$) are stored, in an out-of-order manner, into the first temporary storage 625. As completed positions 1 and 2 are no longer in the active interval 675, bounded and unbounded support characteristics of positions 1 and 2 were transferred from the ring buffer 615 and the first temporary storage 625 to the persistent storage 650. As further shown in FIG. 6B, the bounded support characteristics for position 3, denoted as $\hat{C}$, are transferred from the ring buffer 615 to the persistent storage 650 whereas the unbounded support characteristics for position 3, denoted as $C^°$, are transferred from the first temporary storage 625 to the persistent storage 650, given that completed position 3 is no longer within the active interval 675.

Figure 6C:
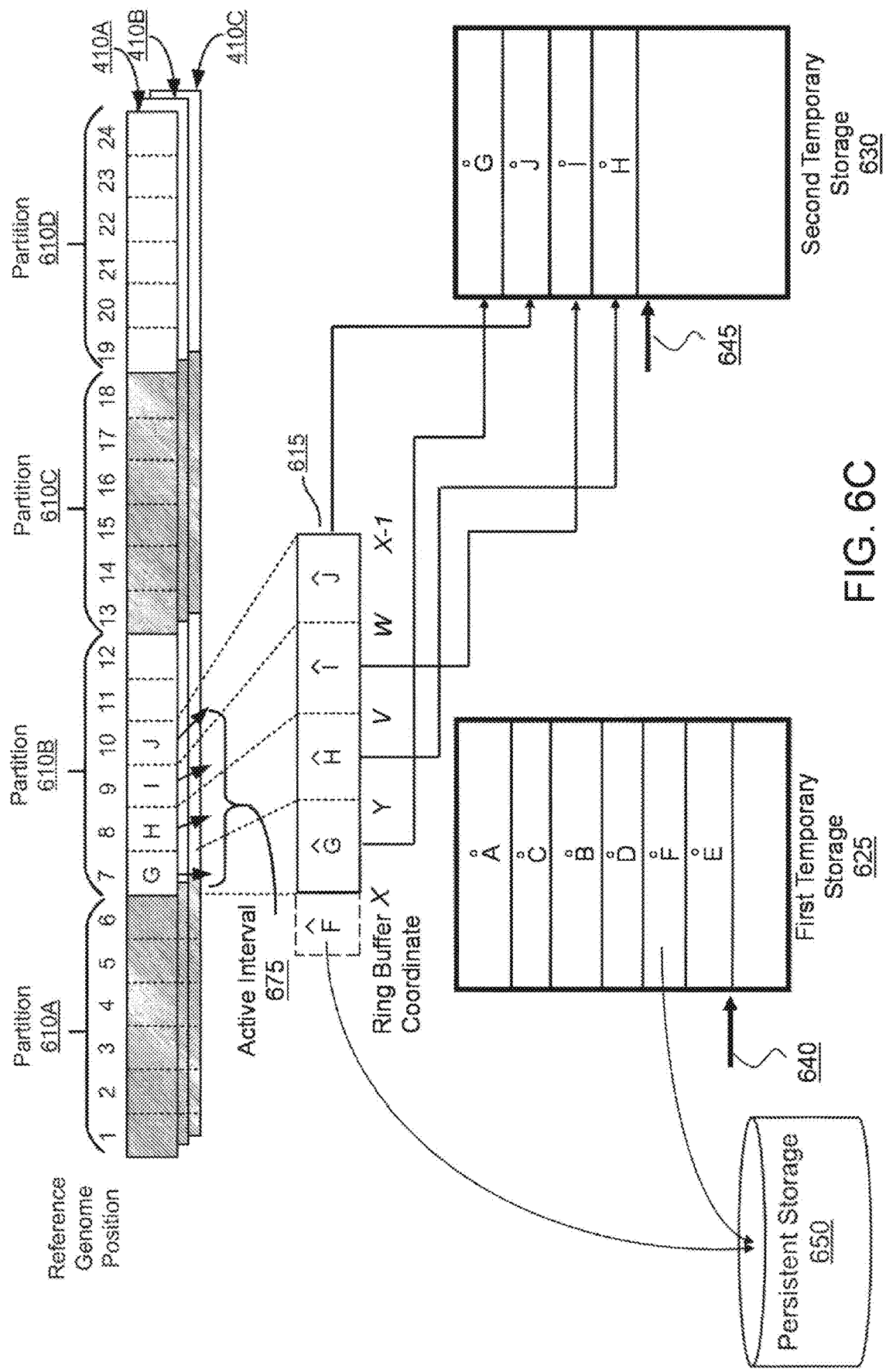
FIG. 6C depicts the storage of support characteristics into persistent storage when the active interval is shifted to be fully located within the second partition, in accordance with various embodiments.

Referring next to FIG. 6C, the active interval 675 is now shifted to be fully located within partition 610B. Here, bounded and unbounded support characteristics of positions 8, 9, and 10 are determined and stored in the ring buffer 615 and the second temporary storage 630. Notably, in this example, the unbounded support characteristics of positions 8, 9, and 10 (denoted as $H^°$, $I^°$, and $J^°$) are stored into the second temporary storage 630 in an out-of-order manner. Additionally, although not shown, the bounded and unbounded support characteristics of positions 4 and 5 are transferred from both the ring buffer 615 and the first temporary storage 625 to the persistent storage 650, given that positions 4 and 5 are no longer in the active interval.

Additionally, bounded and unbounded support characteristics of position 6 (denoted as $\hat{F}$ and $F^\circ$, respectively), are transferred from the ring buffer 615 and the first temporary storage 625 to persistent storage.

Figure 6D:
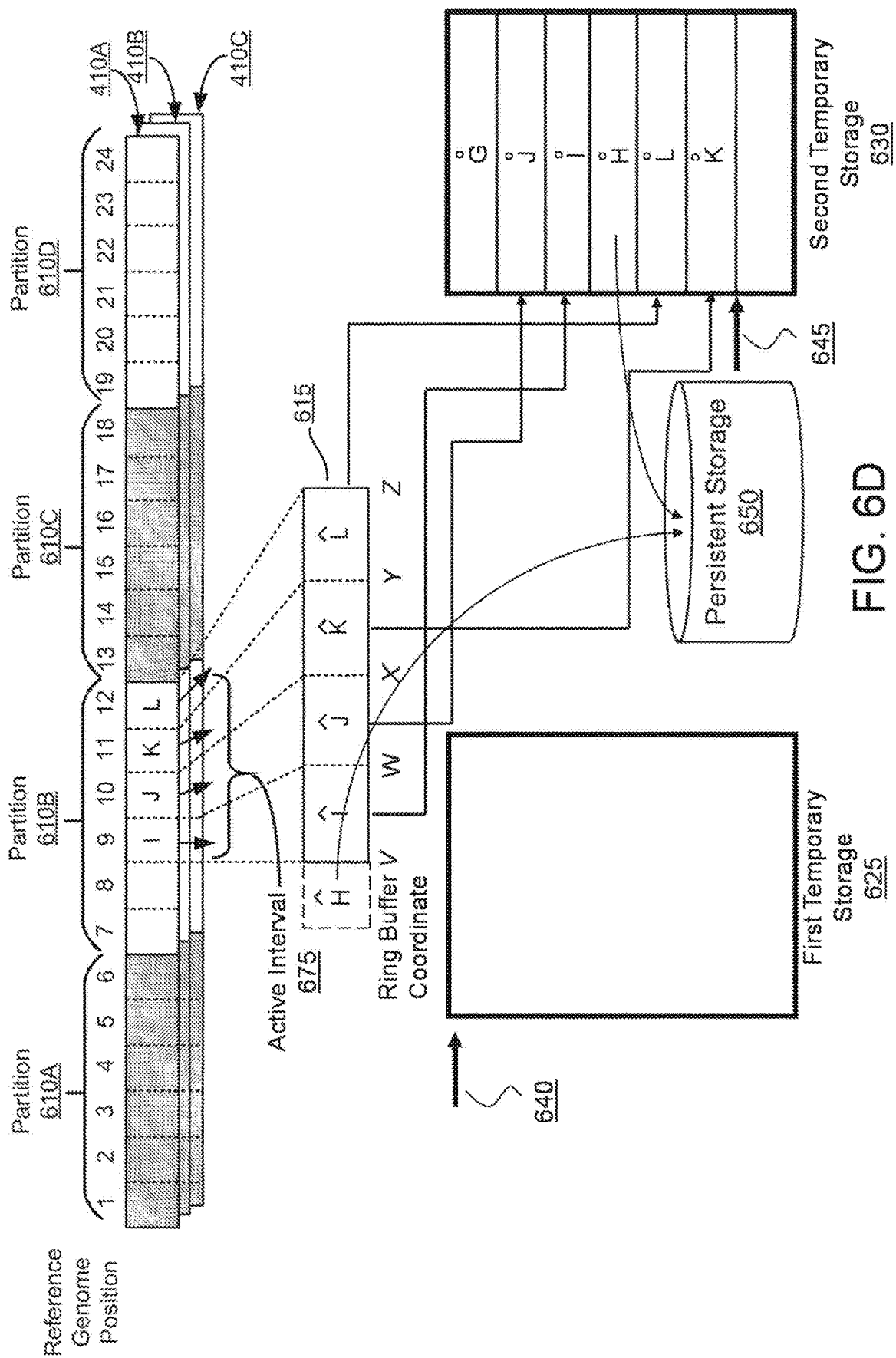
FIG. 6D depicts the storage of support characteristics into persistent storage when the active interval at the second partition is shifted yet fully remains within the second partition, in accordance with various embodiments.

Referring now to FIG. 6D, the active interval 675 is shifted; however, the active interval 675 remains fully within partition 610B. Bounded support characteristics for positions 11 and 12 are determined and stored in the ring buffer 615 and unbounded support characteristics for positions 11 and 12 are stored in the second temporary storage 630 at locations indicated by the memory pointer 645. Here, given that completed positions 7 and 8 are no longer in the active interval 675, the bounded and unbounded support characteristics of positions 7 and 8 are transferred from the ring buffer 615 and second temporary storage 630, respectively, to the persistent storage 650.

Here, given that the support characteristics of all the positions in the first partition 610A (e.g., positions 1-6) have been transferred to persistent storage 650, the memory pointer 640 of the first temporary storage 625 can be reset and the data in the first temporary storage 625 can be erased.

Figure 6E:
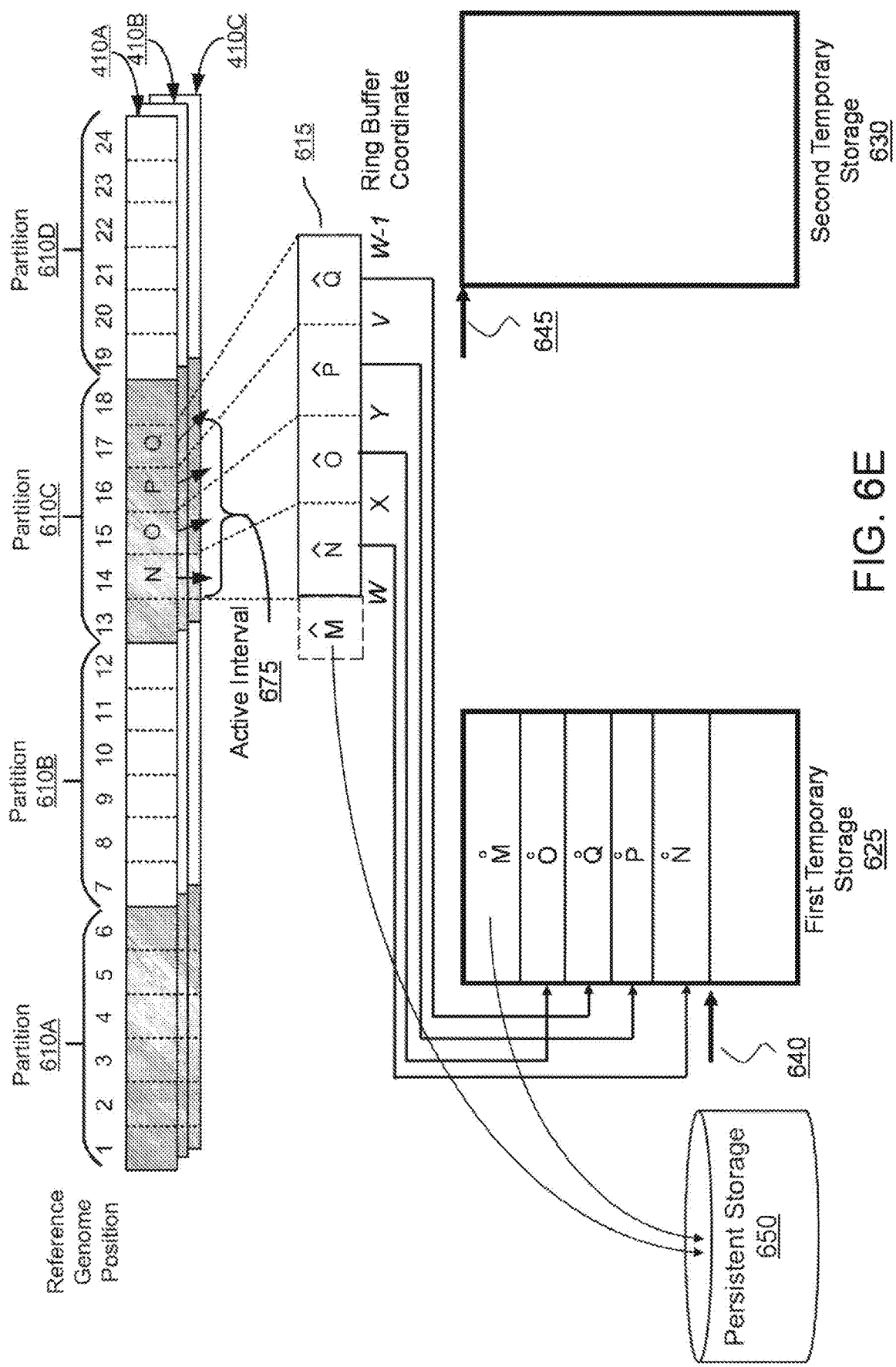
FIG. 6E depicts the storage of support characteristics into persistent storage when the active interval is fully located in a third partition, in accordance with various embodiments.

Referring now to FIG. 6E, the active interval 675 is located fully within partition 610C. Here, an iteration of determining and storing support characteristics of position 13 has been skipped for sake of brevity. As shown in FIG. 6E, bounded support characteristics of positions 14, 15, 16, and 17 are stored into the ring buffer 615 whereas unbounded support characteristics of positions 14-17 are stored into the first temporary storage 625, given that positions 13-16 are in partition 610C. Although not shown, bounded and unbounded support characteristics of positions 9, 10, 11, and 12 are transferred from the ring buffer 615 and the second temporary storage 630 to the persistent storage 650, given that each of completed positions 9, 10, 11, and 12 were no longer in the active interval 675.

Furthermore, given that the support characteristics of all the positions in the second partition 610B (e.g., positions 7-12) have been transferred to the persistent storage 650, the memory pointer 645 of the second temporary storage 630 is reset and the data in the second temporary storage 630 is erased.

The memory allocation process can continue to store support characteristics of positions within subsequent partitions across the reference genome using the ring buffer 615 while alternating between the first temporary storage 625 and the second temporary storage 630.

Figure 7:
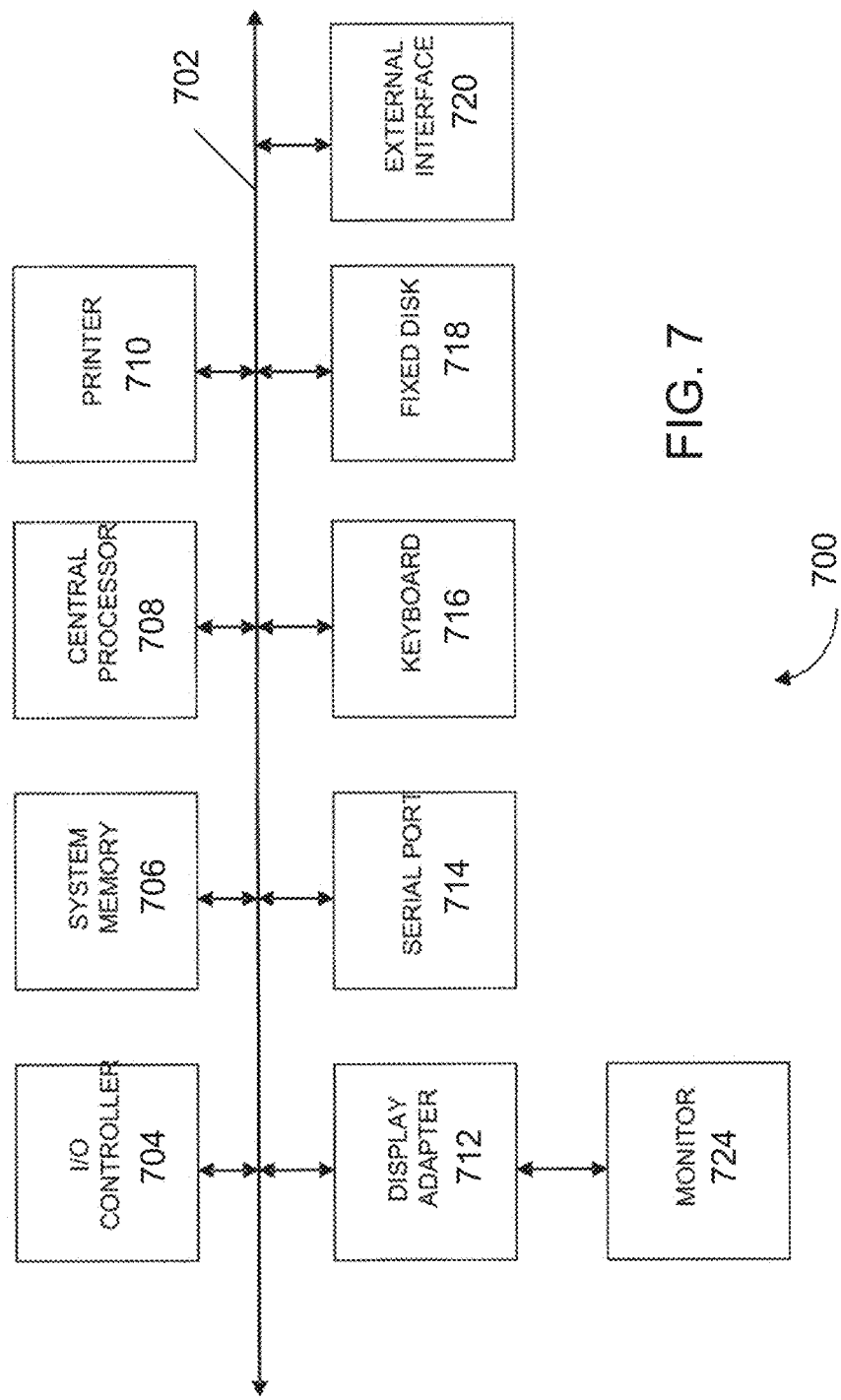
FIG. 7 depicts a block diagram of an example computer system for implementing various systems and methods of the present invention.

Turning now to FIG. 7, components of an example computer system 700 utilized in performing the systems or methods described herein are shown. Any of the systems mentioned herein for performing any of the methods may utilize any suitable number of subsystems. In some embodiments, a computer system includes a single computer apparatus, where the subsystems can be the components of the computer apparatus. In some embodiments, a computer system can include multiple computer apparatuses, each being a subsystem, with internal components.

The subsystems shown in FIG. 7 are interconnected via a system bus 702. Additional subsystems such as a printer 710, keyboard 716, fixed disk 718, monitor 724, which is coupled to display adapter 712, and others are shown. Peripherals and input/output (I/O) devices, which couple to I/O controller 704, can be connected to the computer system by any number of means known in the art, such as serial port 714. For example, serial port 714 or external interface 720 (e.g. Ethernet, Wi-Fi, etc.) can be used to connect computer system 700 to a wide area network such as the Internet, a mouse input device, or a scanner. The interconnection via system bus 792 allows the central processor 708 to communicate with each subsystem and to control the execution of instructions from system memory 706 or the fixed disk 718, as well as the exchange of information between subsystems. The system memory 706 and/or the fixed disk 718 can embody a computer readable medium. Any of the values mentioned herein can be output from one component to another component and can be output to the user.

A computer system can include a plurality of the same components or subsystems, e.g., connected together by external interface 720 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application can be implemented as software code to be executed by a processor using any suitable computer language such as, for example, Java, C++ or Perl using, for example, conventional or object-oriented techniques. The software code can be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium can be any combination of such storage or transmission devices.

Such programs can also be encoded and transmitted using carrier signals adapted for transmission via wired, optical, and/or wireless networks conforming to a variety of protocols, including the Internet. As such, a computer readable medium according to an embodiment of the present invention can be created using a data signal encoded with such programs. Computer readable media encoded with the program code can be packaged with a compatible device or provided separately from other devices (e.g., via Internet download). Any such computer readable medium can reside on or within a single computer program product (e.g. a hard drive, a CD, or an entire computer system), and can be present on or within different computer program products within a system or network. A computer system can include a monitor, printer, or other suitable display for providing any of the results mentioned herein to a user.

Additional Considerations

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Any of the steps, operations, or processes described herein may be performed or implemented with one or more hardware or software modules of the apparatus, alone or in combination with other devices. In one embodiment, a software module is implemented with a computer program product comprising a computer-readable medium containing computer program code, which can be executed by a computer processor for performing any or all of the steps, operations, or processes described.

It will be understood that various details of the present invention may be changed without departing from the scope of the present invention. Furthermore, the foregoing description is for the purpose of illustration only, and not for the purpose of limitation.

What is claimed is:

1. A method for determining support characteristics of positions across a reference genome, the method comprising:

accessing a reference genome sequence expressed in a first format that represents each nucleotide base as a character using a full byte;

accessing a sequence read expressed in a second format that represents each nucleotide base as a numerical value using half a byte;

converting the first format of the reference genome sequence into an internal representation which represents each nucleotide base as a numerical value using a full byte;

converting the second format of the sequence read into the internal representation, wherein the converting comprises:

loading the sequence read into a 16-byte array;

extracting nucleotide bases at even positions and nucleotide bases at odd positions of the sequence read from the 16-byte array using a 16-byte mask;

unpacking and interleaving a lower half of the nucleotide bases at even positions and a lower half of the nucleotide bases at odd positions as first 16 bytes;

unpacking and interleaving a higher half of the nucleotide bases at even positions and a higher half of the nucleotide bases at odd positions as second 16 bytes; and reordering the nucleotide bases in the sequence read by storing the first 16 bytes followed by the second 16 bytes into an output array representing the sequence read in the internal representation;

identifying one or more mismatched nucleotide bases by comparing at least N contiguous nucleotide bases of the sequence read expressed in the internal representation to at least N contiguous nucleotide bases of the reference genome sequence expressed in the internal representation, wherein N is greater than 1.

2. The method of claim 1, wherein the first format is a FASTA format.

3. The method of claim 2, wherein converting the first format of the reference genome sequence into the internal representation comprises:

looking up a M nucleotide bases of the reference genome sequence in a lookup table, wherein M is greater than 1.

4. The method of claim 3, wherein the M is 16, 32, or 64.

5. The method of claim 1, wherein the second format is a binary alignment/map (BAM) format.

6. The method of claim 1, wherein converting the second format of the sequence read into the internal representation further comprises:
expanding each of numerical values represented in half a byte into a full byte.

7. The method of claim 1, wherein the converting the second format of the sequence read into the internal representation is performed in parallel in less than a clock cycle per input byte.

8. The method of claim 1, wherein comparing the sequence read expressed in the internal representation to the reference genome expressed in the internal representation comprises:
performing one of a bitwise exclusive-or (XOR) or AND-NOT operation to compare the N contiguous nucleotide bases.

9. The method of claim 8, wherein performing the bitwise XOR operation comprises:
accessing a concise idiosyncratic gapped alignment report (CIGAR) string of the sequence read, wherein the bitwise XOR operation is performed on a segment of nucleotide bases represented by an alignment matching region indicated by the CIGAR string.

10. The method of claim 1, further comprising:
initializing an array representing positions across the reference genome;
incrementing an entry of the array representing a position corresponding to a first nucleotide base of the sequence read; and
decrementing an entry of the array representing a position corresponding to a last nucleotide base of the sequence read.

11. The method of claim 1, wherein the N is 8, 16, 32, or 64.

12. The method of claim 1, wherein the extracting the nucleotide bases at even positions and the nucleotide bases at odd positions from the 16-byte array using the 16-byte mask comprises:
extracting the nucleotide bases at the odd positions of the sequence read from the 16-byte array by applying the 16-byte mask to the 16-byte array; and
extracting the nucleotide bases at the even positions of the sequence read from the 16-byte array by right-shifting data in the 16-byte array before applying the 16-byte mask.

13. A non-transitory computer-readable medium storing one or more programs, the one or more programs including instructions which, when executed by an electronic device including a processor, cause the device to perform the method of claim 1.

14. An electronic device comprising:
one or more processors;
a memory; and
one or more programs, wherein the one or more programs are stored in the memory and configured to be executed by the one or more processors, the one or more programs including instructions for performing the method of claim 1.

* * * * *

SEQUENCE LISTING

```
<160> NUMBER OF SEQ ID NOS: 2

<210> SEQ ID NO 1
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (14)..(14)
<223> OTHER INFORMATION: n is a, c, g, or t

<400> SEQUENCE: 1
gatgctcgaa gctnca                                              16

<210> SEQ ID NO 2
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 2
gatgctcgaa gctgca                                              16
```